(12) United States Patent
Bicker et al.

(10) Patent No.: US 11,369,586 B2
(45) Date of Patent: Jun. 28, 2022

(54) ANTIFUNGAL PEPTOIDS

(71) Applicant: MIDDLE TENNESSEE STATE UNIVERSITY, Murfreesboro, TN (US)

(72) Inventors: Kevin L. Bicker, Rockvale, TN (US); Madyson P. Middleton, Tennessee Ridge, TN (US); Scott A. Armstrong, Memphis, TN (US)

(73) Assignee: Middle Tennessee State University, Murfreesboro, TN (US)

( * ) Notice: Subject to any disclaimer, the term of this patent is extended or adjusted under 35 U.S.C. 154(b) by 39 days.

(21) Appl. No.: 16/718,577

(22) Filed: Dec. 18, 2019

(65) Prior Publication Data
US 2020/0188354 A1 Jun. 18, 2020

Related U.S. Application Data

(60) Provisional application No. 62/781,474, filed on Dec. 18, 2018.

(51) Int. Cl.
| | |
|---|---|
| *C07C 259/06* | (2006.01) |
| *A61K 31/381* | (2006.01) |
| *A61K 45/06* | (2006.01) |
| *C07D 333/24* | (2006.01) |
| *A61P 31/10* | (2006.01) |

(52) U.S. Cl.
CPC ............ *A61K 31/381* (2013.01); *A61K 45/06* (2013.01); *A61P 31/10* (2018.01); *C07D 333/24* (2013.01)

(58) Field of Classification Search
None
See application file for complete search history.

(56) References Cited

PUBLICATIONS

CLSI. Reference method for broth dilution antifungal susceptibility testing of yeasts; approved standard-third edition; CLSI document M27-A3.; Clinical and Laboratory Standards Institute: Wayne, PA, 2008.
Amblard et al., Methods and protocols of modern solid phase Peptide synthesis. *Mol Biotechnol* 33, 239-254 (2006).
Bolt et al., Exploring the links between peptoid antibacterial activity and toxicity. *Medchemcomm* 8, 886-896 (2017).
Burkoth et al., Incorporation of unprotected heterocyclic side chains into peptoid oligomers via solid-phase submonomer synthesis. *J Am Chem Soc* 125, 8841-8845 (2003).
Chongsiriwatana et al., Short alkylated peptoid mimics of antimicrobial lipopeptides. *Antimicrob Agents Chemother* 55, 417-420 (2011).
Chongsiriwatana et al., Peptoids that mimic the structure, function, and mechanism of helical antimicrobial peptides. *Proc Natl Acad Sci U S A* 105, 2794-2799 (2008).
Chongsiriwatana et al., Functional synergy between antimicrobial peptoids and peptides against Gram-negative bacteria. *Antimicrob Agents Chemother* 55, 5399-5402 (2011).
Corson et al., Discovery and Characterization of a Peptoid with Antifungal Activity against Cryptococcus neoformans. *ACS Med Chem Lett* 7, 1139-1144 (2016).
Culf et al., Solid-phase synthesis of N-substituted glycine oligomers (alpha-peptoids) and derivatives. *Molecules* 15, 5282-5335 (2010).
Datta et al., Spread of Cryptococcus gattii into Pacific Northwest region of the United States. *Emerg Infect Dis* 15, 1185-1191 (2009).
Fisher et al., Peptoid Library Agar Diffusion (PLAD) Assay for the High-Throughput Identification of Antimicrobial Peptoids. *ACS Comb Sci* 18, 287-291 (2016).
Galetti et al., Multicomponent synthesis of acylated short peptoids with antifungal activity against plant pathogens. *Mol Divers* 16, 113-119 (2012).
Hanson et al., In Antimicrobial Drug Resistance: Clinical and Epidemiological Aspects; Mayers, D. L., Ed.; Humana Press: Totowa, NJ, pp. 967-985 (2009).
Kapoor et al., Efficacy of antimicrobial peptoids against *Mycobacterium tuberculosis*. *Antimicrob Agents Chemother* 55, 3058-3062 (2011).
Kapoor et al., Antimicrobial peptoids are effective against Pseudomonas aeruginosa biofilms. *Antimicrob Agents Chemother* 55, 3054-3057 (2011).
Latham, Therapeutic peptides revisited. *Nat Biotechnol* 17, 755-757 (1999).
Lee et al., Effect of side chain hydrophobicity and cationic charge on antimicrobial activity and cytotoxicity of helical peptoids. *Bioorg Med Chem Lett* 28, 170-173 (2018).
Luo et al., Peptoid Efficacy against Polymicrobial Biofilms Determined by Using Propidium Monoazide-Modified Quantitative PCR. *Chembiochem* 18, 111-118 (2017).
Middleton et al., Improved potency and reduced toxicity of the antifungal peptoid AEC5 through submonomer modification. *Bioorg Med Chem Lett* 28, 3514-3519 (2018).
Mojsoska et al., Structure-activity relationship study of novel peptoids that mimic the structure of antimicrobial peptides. *Antimicrob Agents Chemother* 59, 4112-4120 (2015).
Movahed et al., Genome-Wide Transcription Study of Cryptococcus neoformans H99 Clinical Strain versus Environmental Strains. *PLoS One* 10, e0137457 (2015).
Murugan et al., Non hemolytic short peptidomimetics as a new class of potent and broad-spectrum antimicrobial agents. *Bioorg Med Chem Lett* 23, 4633-4636 (2013).
Pappas et al., Clinical practice guidelines for the management of candidiasis: 2009 update by the Infectious Diseases Society of America. *Clin Infect Dis* 48, 503-535 (2009).
Patch et al., Helical peptoid mimics of magainin-2 amide. *J Am Chem Soc* 125, 12092-12093 (2003).

(Continued)

*Primary Examiner* — Sudhakar Katakam
*Assistant Examiner* — Jennifer C Sawyer
(74) *Attorney, Agent, or Firm* — Mueting Raasch Group

(57) ABSTRACT

Described herein are antifungal peptoids, the development and characterization of the antifungal peptoids, methods of making the antifungal peptoids, and methods of using the antifungal peptoids. In some embodiments, the antifungal peptoids may be administered to a subject infected with or at risk of being infected with pathogenic fungi including, for example *Cryptococcus* spp. In some embodiments, the *Cryptococcus* spp. may include *C. neoformans* or *C. gattii* or both.

9 Claims, 7 Drawing Sheets

(56) References Cited

PUBLICATIONS

Perfect et al., Clinical practice guidelines for the management of cryptococcal disease: 2010 update by the infectious diseases society of America. *Clin Infect Dis* 50, 291-322 (2010).

Rajasingham et al., Global burden of disease of HIV-associated cryptococcal meningitis: an updated analysis. *Lancet Infect Dis* 17, 873-881 (2017).

Ren et al., Fragmentation Patterns and Mechanisms of Singly and Doubly Protonated Peptoids Studied by Collision Induced Dissociation. *J Am Soc Mass Spectrom* 27, 646-661 (2016).

Smith et al., Treatment and outcomes among patients with Cryptococcus gattii infections in the United States Pacific Northwest. *PLoS One* 9, e88875 (2014).

Turkett et al., Evaluating the Effect of Peptoid Lipophilicity on Antimicrobial Potency, Cytotoxicity, and Combinatorial Library Design. *ACS Comb Sci* 19, 229-233 (2017).

Walsh et al., Treatment of aspergillosis: clinical practice guidelines of the Infectious Diseases Society of America. *Clin Infect Dis* 46, 327-360 (2008).

Zasloff, Antimicrobial peptides of multicellular organisms. *Nature* 415, 389-395 (2002).

Zhang et al., Antimicrobial peptides: therapeutic potential. *Expert Opin Pharmacother* 7, 653-663 (2006).

Zuckermann et al., Efficient method for the preparation of peptoids [oligo(N-substituted glycines)] by submonomer solid-phase synthesis, *J. Am. Chem. Soc.* 114(26), 10646-10647 (1992).

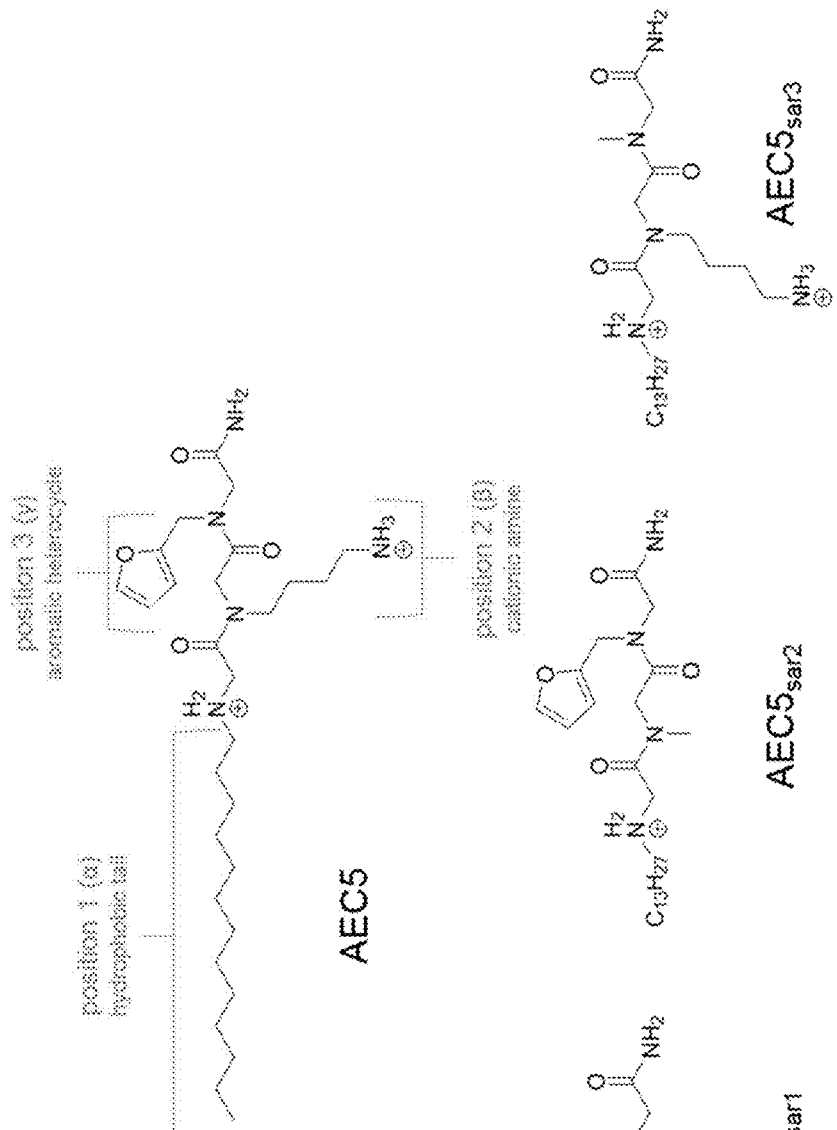

| Compound | MW (g/mol) | LogD_{7.4} | C. neoformans MIC (µg/mL) | HepG2 TD_{50} (µg/mL) | SR |
|---|---|---|---|---|---|
| AEC5 | 521.8 | -1.18 | 6.3 | 56.2 | 9 |
| α-1 | 563.8 | 0.16 | 3.13 | 40.4 | 13 |
| α-2 | 479.7 | -2.51 | 400 | ND | ND |
| α-3 | 451.6 | -3.4 | >800 | ND | ND |
| α-4 | 543.8 | -1.11 | 100 | 800 | 8 |
| α-5 | 475.6 | -2.77 | 400 | ND | ND |

| Compound | MW (g/mol) | LogD$_{7.4}$ | C. neoformans MIC (μg/mL) | HepG2 TD$_{50}$ (μg/mL) | SR |
|---|---|---|---|---|---|
| AEC5 | 521.8 | -1.18 | 6.3 | 56.2 | 8.9 |
| γ-8 | 559.8 | -0.25 | 400 | ND | ND |
| γ-9 | 571.8 | -1.99 | 100 | ND | ND |
| γ-10 | 606.9 | 0.22 | 100 | ND | ND |

| Compound | MW (g/mol) | LogD$_{7.4}$ | C. neoformans MIC (μg/mL) | HepG2 TD$_{50}$ (μg/mL) | SR |
|---|---|---|---|---|---|
| AEC5 | 521.8 | -1.18 | 6.3 | 56.2 | 9 |
| γ-1 | 521.8 | -2.31 | 25 | 147.2 | 6 |
| γ-2 | 537.8 | -0.32 | 3.13 | 79.3 | 25 |
| γ-3 | 549.8 | -2.06 | 50 | 228.3 | 5 |
| γ-4 | 584.9 | 0.15 | 3.13 | 42.7 | 14 |
| γ-5 | 532.8 | -1.46 | 25 | 104.1 | 4 |
| γ-6 | 531.8 | -0.24 | 3.13 | 52.2 | 17 |
| γ-7 | 525.8 | -1.54 | 12.5 | 170.4 | 14 |

| Compound | MW (g/mol) | LogD$_{7.4}$ | C. neoformans MIC (µg/mL) | HepG2 TD$_{50}$ (µg/mL) | SR |
|---|---|---|---|---|---|
| γ-2 | 537.8 | -0.32 | 3.13 | 79.3 | 25 |
| β-1 | 523.8 | -0.73 | 3.13 | 47.3 | 15 |
| β-2 | 509.8 | 0.03 | 6.25 | 40.5 | 6 |
| β-3 | 565.4 | 0.35 | 3.13 | 56.2 | 18 |
| β-4 | 565.8 | -1.16 | 12.5 | 40.8 | 3 |
| β-5 | 580.9 | -1.28 | 3.13 | 91.2 | 29 |
| β-6 | 538.8 | 2.18 | 12.5 | 31 | 3 |

FIG. 7A

| Compound | Position 1 | Position 2 | Position 3 |
|---|---|---|---|
| AEC5sar1 | Sar | NLys(Boc) | Nfur |
| AEC5sar2 | Ntri | Sar | Nfur |
| AEC5sar3 | Ntri | NLys(Boc) | Sar |
| α-1 | Nhda | NLys(Boc) | Nfur |
| α-2 | Ndec | NLys(Boc) | Nfur |
| α-3 | Noct | NLys(Boc) | Nfur |
| α-4 | Nfar | NLys(Boc) | Nfur |
| α-5 | Nct | NLys(Boc) | Nfur |
| γ-1 | Ntri | NLys(Boc) | Nami |
| γ-2 | Ntri | NLys(Boc) | Ntma |
| γ-3 | Ntri | NLys(Boc) | Napi |
| γ-4 | Ntri | NLys(Boc) | NhTrp |
| γ-5 | Ntri | NLys(Boc) | Npyr |
| γ-6 | Ntri | NLys(Boc) | NPhe |
| γ-7 | Ntri | NLys(Boc) | Nhhf |
| γ-8 | Nfar | NLys(Boc) | Ntma |
| γ-9 | Nfar | NLys(Boc) | Napi |
| γ-10 | Nfar | NLys(Boc) | NhTrp |
| β-1 | Ntri | Nap(Boc) | Ntma |
| β-2 | Ntri | Nae(Boc) | Ntma |
| β-3 | Ntri | Nah(Boc) | Ntma |
| β-4 | Ntri | Nap(Mmt) | Ntma |
| β-5 | Ntri | NLys(Mmt) | Ntma |
| β-6 | Ntri | Nabol(TBDMS) | Ntma |

FIG. 7B

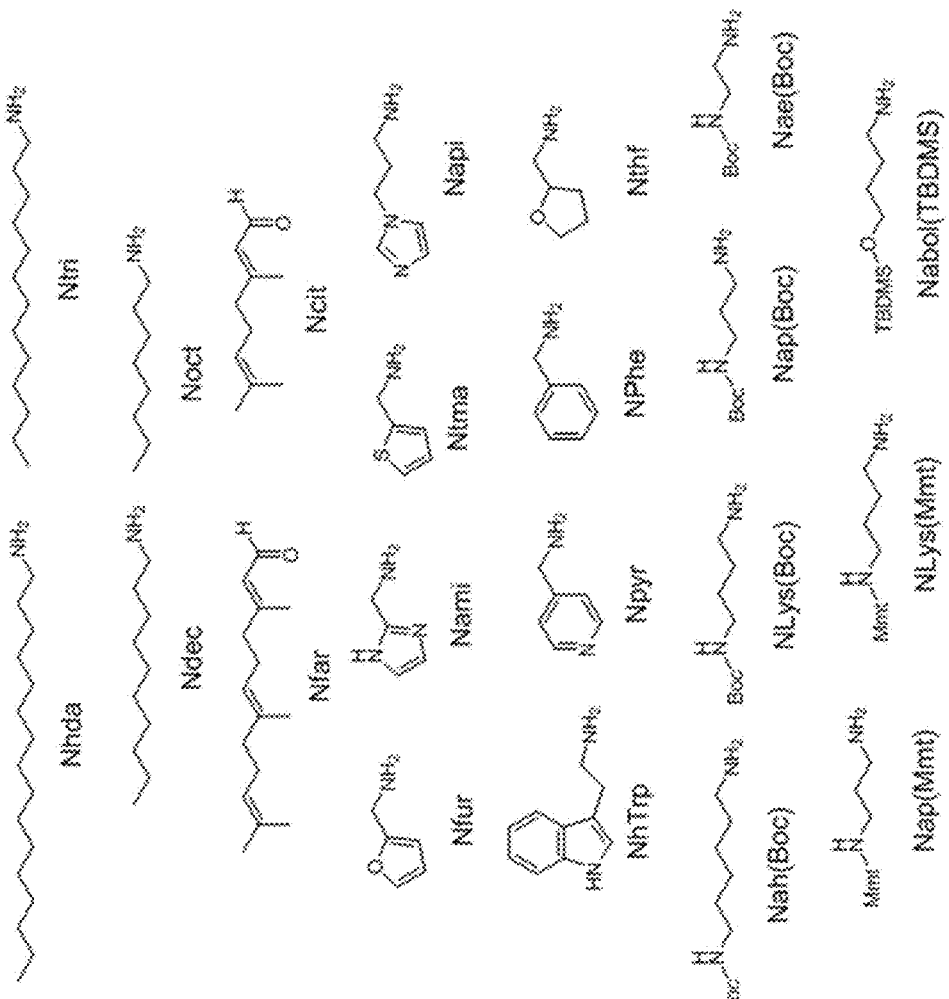

ANTIFUNGAL PEPTOIDS

CONTINUING APPLICATION DATA

This application claims the benefit of U.S. Provisional Application Ser. No. 62/781,474, filed Dec. 18, 2018, which is incorporated by reference herein.

GOVERNMENT FUNDING

This invention was made with government support under 112861 awarded by National Institutes of Health. The government has certain rights in the invention.

BACKGROUND

*Cryptococcus neoformans* is a common infectious agent among immunocompromised individuals, such as transplant patients and those infected with HIV/AIDS. Initial infection of this yeast-like fungus occurs in the pulmonary system with central nervous system infection following, leading to cryptococcal meningitis. (Movahed, et al. *PLoS One* 2015, 10 (9), e0137457.) The most recent estimates indicate that roughly 220,000 HIV/AIDS patients contract cryptococcal meningitis from *C. neoformans* each year and that over 181,000 (82%) of these cases will be fatal. (Rajasingham et al. *Lancet Infect. Dis.* 2017, 17 (8), 873-881.) A second species of *Cryptococcus, C. gattii*, which is endemic to parts of the South Pacific has been observed to cause pulmonary cryptococcosis, cryptococcal meningitis, and cerebral cryptococcosis. *C. gattii* caused a recent outbreak in the Pacific Northwest regions of Canada and the United States, and has the capacity to infect both immunocompromised and immunocompetent individuals. (Smith et al. *PLoS One* 2014, 9 (2), e88875; Datta et al. *Emerg. Infect. Dis.* 2009, 15 (8), 1185.)

Treatment for infections due to pathogenic fungi, such as *Cryptococcus* spp. vary significantly with the species of the microorganism and the immune status of the patient. Current clinical antifungal agents include amphotericin B, azoles (for example, fluconazole, itraconazole), echinocandins (for example, caspofungin, micafungin), and flucytosine. First-line treatments, such as flucytosine, and fluconazole, as well as last-line treatments, such as amphotericin B each carry their own risks, including high mammalian cytotoxicity that results in gastrointestinal complications, vomiting, QT prolongation, and/or hepatitis. (Pappas et al. *Clin. Infect. Dis.* 2009, 48 (5), 503-535; Perfect et al. *Clin. Infect. Dis.* 2010, 50 (3), 291-322; Walsh et al. *Clin. Infect. Dis.* 2008, 46 (3), 327-360.) Moreover, some organisms have developed resistance to a number of these drugs. General practice is to give these drugs in combination over extended periods of time due to increasingly observed resistance in many fungal pathogens, thereby exacerbating the cytotoxic effects and increasing the likelihood of resistance development. (Perfect et al. *Clin. Infect. Dis.* 2010, 50 (3), 291-322; Hanson et al. In *Antimicrobial Drug Resistance: Clinical and Epidemiological Aspects*; Mayers, D. L., Ed.; Humana Press: Totowa, N.J., 2009; pp 967-985.) Considering the dearth of suitable treatments, new therapeutic options for patients dealing with fungal infections would be advantageous.

SUMMARY OF THE INVENTION

This disclosure describes antifungal peptoids, the development and characterization of the antifungal peptoids, methods of making the antifungal peptoids, and methods of using the antifungal peptoids. In some embodiments, the antifungal peptoids may be administered to a subject infected with or at risk of being infected with pathogenic fungi including, for example *Cryptococcus* spp. In some embodiments, the *Cryptococcus* spp. may include *C. neoformans* or *C. gattii* or both.

In one aspect, this disclosure describes a composition including one or more of the compounds of Table 1.

In another aspect, this disclosure describes a composition including γ-2:

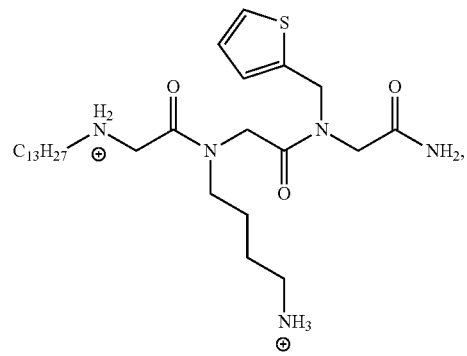

or β-5:

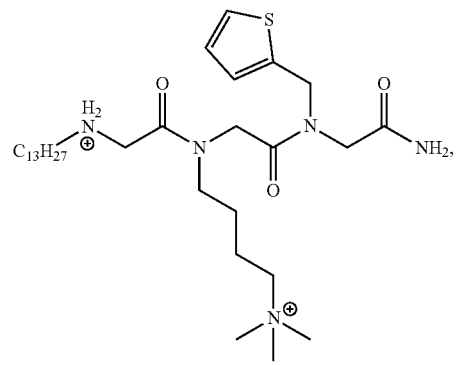

or both.

In some embodiments, the composition includes a pharmaceutical composition. In some embodiments, the composition includes a pharmaceutically acceptable carrier.

In another aspect, this disclosure describes a method that includes administering to a subject a composition described herein. In some embodiments, the subject is an animal. In some embodiments, the subject is a human.

In some embodiments, the method includes treating or preventing a fungal infection in the subject including, for example, infection with a *Cryptococcus* spp. A *Cryptococcus* spp. may include *Cryptococcus neoformans*, or *Cryptococcus gattii*, or both.

In some embodiments, the method further includes administering an effective amount of a systemic antifungal agent or a topical antifungal agent.

In some embodiments, the method further includes administering an effective amount of an azole, a polyene, an echinocandin, or 5-fluorocytosine.

In another aspect, this disclosure describes a compound having the formula:

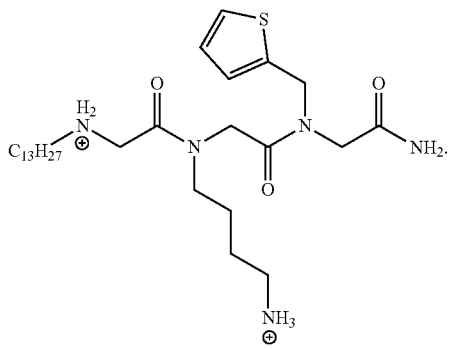

In a further aspect, this disclosure describes a compound having the formula:

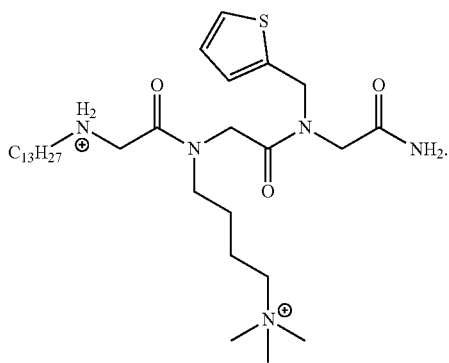

In yet another aspect, this disclosure described a method of making a compound having the formula:

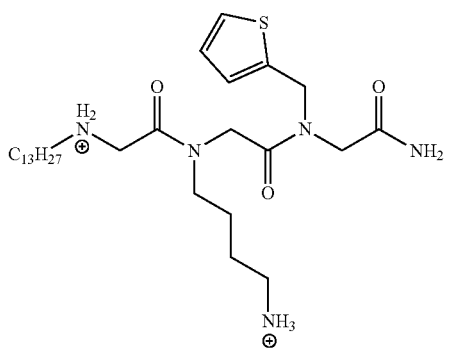

or a compound having the formula:

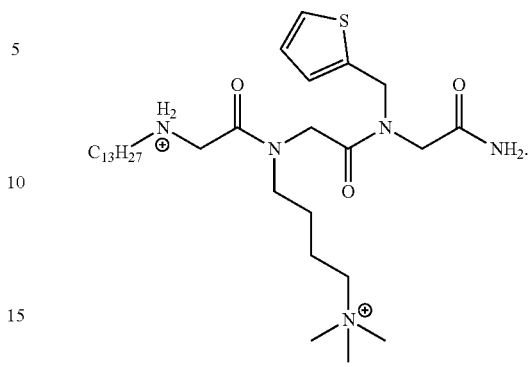

In some embodiments, the method includes submonomer peptoid synthesis.

The words "preferred" and "preferably" refer to embodiments of the invention that may afford certain benefits, under certain circumstances. However, other embodiments may also be preferred, under the same or other circumstances. Furthermore, the recitation of one or more preferred embodiments does not imply that other embodiments are not useful and is not intended to exclude other embodiments from the scope of the invention.

The terms "comprises" and variations thereof do not have a limiting meaning where these terms appear in the description and claims.

The term "consisting of" means including, and limited to, whatever follows the phrase "consisting of." That is, "consisting of" indicates that the listed elements are required or mandatory, and that no other elements may be present.

The term "consisting essentially of" indicates that any elements listed after the phrase are included, and that other elements than those listed may be included provided that those elements do not interfere with or contribute to the activity or action specified in the disclosure for the listed elements.

Unless otherwise specified, "a," "an," "the," and "at least one" are used interchangeably and mean one or more than one.

Also herein, the recitations of numerical ranges by endpoints include all numbers subsumed within that range (for example, 1 to 5 includes 1, 1.5, 2, 2.75, 3, 3.80, 4, 5, etc.).

For any method disclosed herein that includes discrete steps, the steps may be conducted in any feasible order. And, as appropriate, any combination of two or more steps may be conducted simultaneously.

All headings are for the convenience of the reader and should not be used to limit the meaning of the text that follows the heading, unless so specified.

Reference throughout this specification to "one embodiment," "an embodiment," "certain embodiments," or "some embodiments," etc., means that a particular feature, configuration, composition, or characteristic described in connection with the embodiment is included in at least one embodiment of the disclosure. Thus, the appearances of such phrases in various places throughout this specification are not necessarily referring to the same embodiment of the disclosure. Furthermore, the particular features, configurations, compositions, or characteristics may be combined in any suitable manner in one or more embodiments.

Unless otherwise indicated, all numbers expressing quantities of components, molecular weights, and so forth used in the specification and claims are to be understood as being modified in all instances by the term "about." Accordingly, unless otherwise indicated to the contrary, the numerical parameters set forth in the specification and claims are approximations that may vary depending upon the desired properties sought to be obtained by the present invention. At the very least, and not as an attempt to limit the doctrine of equivalents to the scope of the claims, each numerical parameter should at least be construed in light of the number of reported significant digits and by applying ordinary rounding techniques.

Notwithstanding that the numerical ranges and parameters setting forth the broad scope of the invention are approximations, the numerical values set forth in the specific examples are reported as precisely as possible. All numerical values, however, inherently contain a range necessarily resulting from the standard deviation found in their respective testing measurements.

The above summary of the present invention is not intended to describe each disclosed embodiment or every implementation of the present invention. The description that follows more particularly exemplifies illustrative embodiments. In several places throughout the application, guidance is provided through lists of examples, which examples may be used in various combinations. In each instance, the recited list serves only as a representative group and should not be interpreted as an exclusive list.

BRIEF DESCRIPTION OF THE FIGURES

FIG. 1A shows the structure of the antifungal tripeptoid AEC5, showing distinct functionalities at each of the three submonomer positions. FIG. 1B shows compound structures for the sarcosine scan of AEC5, where the submonomer at each position was replaced with sarcosine. FIG. 1C shows calculated distribution coefficient (c Log $D_{7.4}$), $C.$ $neoformans$ antifungal potency (MIC), and HepG2 liver cell toxicity ($TD_{50}$) for AEC5 and AEC5 sarcosine scan compounds. MW=molecular weight; c Log $D_{7.4}$=calculated distribution coefficient at pH 7.4; MIC=minimum inhibitory concentration; $TD_{50}$=toxic dose 50%; SR=selectivity ratio ($TD_{50}$/MIC); ND=not determined.

FIG. 7A-FIG. 7B show a table and structures, respectively, of the amines used for the synthesis of each peptoid.

DETAILED DESCRIPTION OF ILLUSTRATIVE EMBODIMENTS

Figures 2A, 2B:
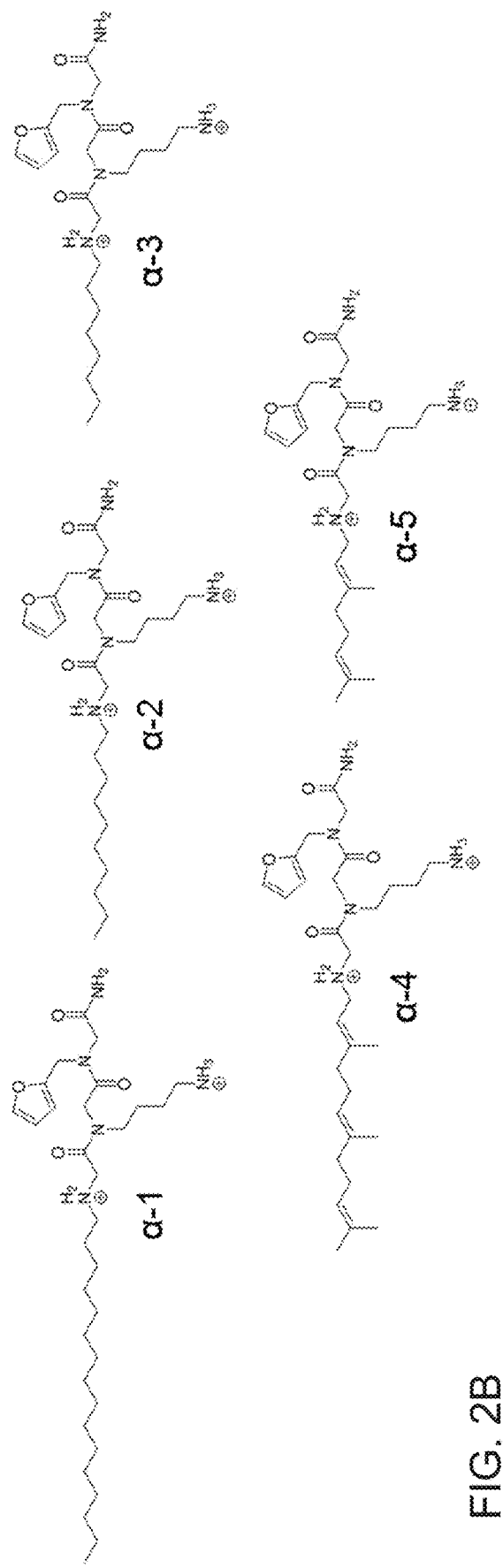
FIG. 2A shows Round 1 SAR compounds ($\alpha$-1, $\alpha$-2, $\alpha$-3, $\alpha$-3, and $\alpha$-5) with varied hydrophobic tails in the first position.
FIG. 2B shows calculated distribution coefficient (c Log $D_{7.4}$), $C.$ $neoformans$ antifungal potency (MIC), and HepG2 liver cell toxicity ($TD_{50}$) for Round 1 SAR compounds. MW=molecular weight; c Log $D_{7.4}$=calculated distribution coefficient at pH 7.4; MIC=minimum inhibitory concentration; $TD_{50}$=toxic dose 50%; SR=selectivity ratio ($TD_{50}$/MIC); ND=not determined.

Described herein are antifungal peptoids, the development and characterization of the antifungal peptoids, methods of making the antifungal peptoids, and methods of using the antifungal peptoids. In some embodiments, the antifungal peptoids may be administered to a subject infected with or at risk of being infected with pathogenic fungi including, for example $Cryptococcus$ spp. In some embodiments, the $Cryptococcus$ spp. may include $C.$ $neoformans$ or $C.$ $gattii$ or both.

Antimicrobial Peptides and Peptoids

Many organisms use antimicrobial peptides (AMPs) as a part of their innate immune response against pathogenic bacteria and fungi. (Zasloff, M. $Nature$ 2002, 415(6870), 389-395.) AMPs may be advantageous as clinical antimicrobial agents given their relatively high specificity for microorganisms over mammalian cells and lack of observed drug resistance, likely stemming from their generally accepted mode of action. Most AMPs used against fungi target the cell membrane, forming pores or causing changes in cell permeability that result in a leakage of cytoplasmic components, ultimately resulting in pathogen death. (Id.) These AMPs are able to take advantage of key differences between mammalian and fungal cell membranes, such as ergosterol, a principle sterol only present in fungal cell membranes, to selectively target the pathogen. (Walsh et al. $Clin.$ $Infect.$ $Dis.$ 2008, 46 (3), 327-360.) But peptides are readily recognized and degraded by proteases and are poor clinical therapeutics for combating in vivo fungal infections. (Latham. $Nat.$ $Biotech.$ 1999, 17(8), 755-757; Zhang et al. $Expert$ $Opin.$ $Pharmacother.$ 2006, 7(6), 653-663.)

One means of resolving the proteolytic instability of AMPs involves the use of N-substituted glycines, also referred to as peptoids. In peptides the side chain R group is attached to the $\alpha$-carbon, whereas in peptoids the R group is attached to the amide nitrogen. This alteration in structure makes peptoids unrecognizable by proteases while maintaining many of the advantageous properties of peptides and extending in vivo half-life. (Culf et al. $Molecules$ 2010, 15(8), 5282-5335; Zuckermann et al. $J.$ $Am.$ $Chem.$ $Soc.$ 1992, 114(26), 10646-10647.) The antimicrobial utility of peptoids has been demonstrated against both bacteria and fungi.

Antifungal Peptoid

In one aspect, this disclosure describes an antifungal peptoid. In some embodiments, the antifungal peptoid includes a compound of Table 1 (the structures of which are shown in FIG. 1-FIG. 5). In some embodiments, the antifungal peptoid includes a combination (for example, a mixture) of the compounds of Table 1.

In some embodiments, the antifungal peptoid preferably includes γ-2:

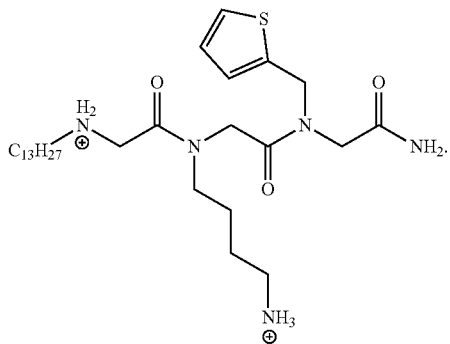

In some embodiments, the antifungal peptoid preferably includes β-5:

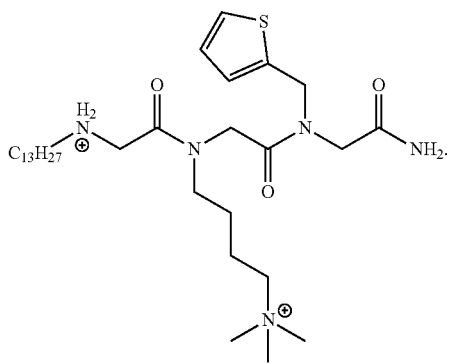

In some embodiments, the antifungal peptoid includes γ-2 and β-5.

In some embodiments the antifungal peptoid has a minimum inhibitory concentration (MIC) against *C. neoformans* of less than 5 μg/mL, less than 4 μg/mL, or less than 3.5 μg/mL. In some embodiments, the antifungal peptoid has a toxicity dose 50% ($TD_{50}$) against HepG2 liver cells, evaluated as described in Example 1, of at least 60 μg/mL, at least 70 μg/mL, at least 75 μg/mL, at least 80 μg/mL, at least 85 μg/mL, at least 90 μg/mL, at least 95 μg/mL, at least 100 μg/mL, at least 150 μg/mL, or at least 200 μg/mL. For example, γ-2 exhibits a MIC against *C. neoformans*, evaluated as described in Example 1, of less than 3.5 μg/mL and a $TD_{50}$ against HepG2 liver cells of at least 75 μg/mL. For example, β-5 exhibits a MIC against *C. neoformans* of less than 3.5 μg/mL and a $TD_{50}$ against HepG2 liver cells of at least 90 μg/mL.

Using a high-throughput screening assay, a peptoid termed AEC5 with potency against *C. neoformans* similar to that of first-line clinical antifungals was recently identified. (Corson et al. *ACS Med. Chem. Lett.* 2016, 7(12):1139-1144.) AEC5 demonstrated relatively minimal toxicity against several mammalian cell types and excellent in vitro proteolytic stability. Example 1 of this disclosure describes the development of peptoids from AEC5 through sequential optimization of each peptoid submonomer by an iterative structure activity relationship (SAR) process.

As further described in Example 1, a sarcosine scan was used to identify the most pharmacophorically important peptoid building blocks of AEC5, followed by sequential optimization of each building block. From this study, two antifungal peptoids, γ-2 and β-5, were identified as particularly advantageous (exhibiting an increase in antifungal potency, as measured using *C. neoformans*, and a decrease in mammalian toxicity, as measured using HepG2 liver cells, resulting in a higher selectivity ratio). These compounds are relatively small and exhibit improved potency towards *Cryptococcus neoformans* compared to AEC5 and decreased toxicity towards mammalian cells compared to AEC5.

Methods of Making the Antifungal Peptoid

In a further aspect, this disclosure describes methods of making an antifungal peptoid as described herein. In some embodiments, the method includes using deprotected Rink Amide polystyrene resin.

In some embodiments, the method includes traditional submonomer peptoid synthesis techniques using bromoacetic acid and diisopropylcarbodiimide for the acylation step and the appropriate amine for the amination step. Appropriate amines for γ-2 are 2-thiophenemethylamine, N-Boc-1,4-diaminobutane, and tridecylamine. Dimethylformamide was used as the solvent throughout synthesis. Final compound was removed from the resin using trifluoroacetic acid and purified by reverse phase HPLC.

In some embodiments, the method includes traditional submonomer peptoid synthesis techniques using bromoacetic acid and diisopropylcarbodiimide for the acylation step and the appropriate amine for the amination step. Appropriate amines for β-5 include 2-thiophenemethylamine, N-monomethoxytrityl-1-1,4-diaminobutane, and tridecylamine. Trimethylation of the second position side chain may be achieved using methyl iodide following Boc protection of the N-terminus and monomethoxytrityl removal with 1% trifluoroacetic acid in dichloromethane. In some embodiments, dimethylformamide may be used as a solvent. In some embodiments, the final compound may be removed from the resin using trifluoroacetic acid. In some embodiments, the final compound may be purified by reverse phase HPLC.

Methods of Using the Antifungal Peptoid

In another aspect, this disclosure describes methods of using an antifungal peptoid as described herein.

In some embodiments, the method includes treating or preventing a fungal infection in a subject. The fungal infection may include an infection with *Candida* spp. and/or *Cryptococcus* spp.

In some embodiments, this disclosure describes a method that includes administering to a subject a composition (including, for example, a pharmaceutical composition) that includes an effective amount of an antifungal peptoid. For example, in some embodiments, the method may include administering to a subject a composition that includes an effective amount of γ-2 and/or β-5. In some embodiments, the subject may be infected with pathogenic fungi including, for example *Cryptococcus* spp. In some embodiments, the *Cryptococcus* spp. may include *C. neoformans, C. gattii*, or both.

Pharmaceutical Compositions

In some aspects, the present disclosure provides a pharmaceutical composition that includes as an active agent an antifungal peptoid as described herein, and a pharmaceutically acceptable carrier. In some embodiments, the antifungal peptoid is γ-2 and/or β-5. The active agent is formulated in a pharmaceutical composition and then, in accordance with the method of the invention, administered to a vertebrate, particularly mammal, such as a human patient, companion animal, or domesticated animal, in a variety of forms adapted to the chosen route of administration. The formulations include those suitable for oral, rectal, vaginal, topical, nasal, ophthalmic or parenteral (including subcutaneous, intramuscular, intraperitoneal, and intravenous) administration.

The pharmaceutically acceptable carrier may include, for example, an excipient, a diluent, a solvent, an accessory ingredient, a stabilizer, a protein carrier, or a biological compound. Non-limiting examples of a protein carrier includes keyhole limpet hemocyanin (KLH), bovine serum albumin (BSA), ovalbumin, or the like. Non-limiting examples of a biological compound which may serve as a carrier include a glycosaminoglycan, a proteoglycan, and albumin. The carrier may be a synthetic compound, such as dimethyl sulfoxide or a synthetic polymer, such as a polyalkyleneglycol. Ovalbumin, human serum albumin, other proteins, polyethylene glycol, or the like may be employed as the carrier. In a preferred embodiment, the pharmaceutically acceptable carrier includes at least one compound that is not naturally occurring or a product of nature.

In some embodiments, the antifungal peptoid is formulated in combination with one or more additional active agents, such an antifungal compound. Any known therapeutic agent may be included as an additional active agent. The action of the additional active agent in the combination therapy may be cumulative to the antifungal peptoid or it may be complementary, for example to manage side effects or other aspects of the patient's medical condition. In one embodiment, the combination therapy includes at least one compound that is not naturally occurring or a product of nature. In some embodiments, the combination therapy includes an azole, a polyene, 5-fluorocytosine, and/or an echinocandin.

The formulations may be conveniently presented in unit dosage form and may be prepared by any of the methods well-known in the art of pharmacy. In some embodiments, a method includes the step of bringing the active agent into association with a pharmaceutical carrier. In general, the formulations are prepared by uniformly and intimately bringing the active compound into association with a liquid carrier, a finely divided solid carrier, or both, and then, if necessary, shaping the product into the desired formulations.

Formulations of the present disclosure suitable for oral administration may be presented as discrete units such as tablets, troches, capsules, lozenges, wafers, or cachets, each containing a predetermined amount of the active agent as a powder or granules, as liposomes, or as a solution or suspension in an aqueous liquor or non-aqueous liquid such as a syrup, an elixir, an emulsion, or a draught. The tablets, troches, pills, capsules, and the like may also contain one or more of the following: a binder such as gum tragacanth, acacia, corn starch or gelatin; an excipient such as dicalcium phosphate; a disintegrating agent such as corn starch, potato starch, alginic acid, and the like; a lubricant such as magnesium stearate; a sweetening agent such as sucrose, fructose, lactose, or aspartame; and a natural or artificial flavoring agent. When the unit dosage form is a capsule, it may further contain a liquid carrier, such as a vegetable oil or a polyethylene glycol. Various other materials may be present as coatings or to otherwise modify the physical form of the solid unit dosage form. For instance, tablets, pills, or capsules may be coated with gelatin, wax, shellac, sugar, and the like. A syrup or elixir may contain one or more of a sweetening agent, a preservative such as methyl- or propylparaben, an agent to retard crystallization of the sugar, an agent to increase the solubility of any other ingredient, such as a polyhydric alcohol, for example glycerol or sorbitol, a dye, and flavoring agent. The material used in preparing any unit dosage form is substantially nontoxic in the amounts employed. The active agent may be incorporated into preparations and devices in formulations that may or may not be designed for sustained release.

Formulations suitable for parenteral administration conveniently include a sterile aqueous preparation of the active agent, or dispersions of sterile powders of the active agent, which are preferably isotonic with the blood of the recipient. Parenteral administration of an antifungal peptoid (e. g., through an intravenous drip) is one form of administration. Isotonic agents that may be included in the liquid preparation include sugars, buffers, and sodium chloride. Solutions of the active agent may be prepared in water, optionally mixed with a nontoxic surfactant. Dispersions of the active agent may be prepared in water, ethanol, a polyol (such as glycerol, propylene glycol, liquid polyethylene glycols, and the like), vegetable oils, glycerol esters, and mixtures thereof. The ultimate dosage form is sterile, fluid, and stable under the conditions of manufacture and storage. The necessary fluidity may be achieved, for example, by using liposomes, by employing the appropriate particle size in the case of dispersions, or by using surfactants. Sterilization of a liquid preparation may be achieved by any convenient method that preserves the bioactivity of the active agent, preferably by filter sterilization. Preferred methods for preparing powders include vacuum drying and freeze drying of the sterile injectable solutions. Subsequent microbial contamination may be prevented using various antimicrobial agents, for example, antibacterial, antiviral and antifungal agents including parabens, chlorobutanol, phenol, sorbic acid, thimerosal, and the like. Absorption of the active agents over a prolonged period may be achieved by including agents for delaying, for example, aluminum monostearate and gelatin.

Nasal spray formulations include purified aqueous solutions of the active agent with preservative agents and isotonic agents. Such formulations are preferably adjusted to a pH and isotonic state compatible with the nasal mucous membranes. Formulations for rectal or vaginal administration may be presented as a suppository with a suitable carrier such as cocoa butter, or hydrogenated fats or hydrogenated fatty carboxylic acids. Ophthalmic formulations are prepared by a similar method to the nasal spray, except that the pH and isotonic factors are preferably adjusted to match that of the eye. Topical formulations include the active agent dissolved or suspended in one or more media such as mineral oil, petroleum, polyhydroxy alcohols, or other bases used for topical pharmaceutical formulations. Topical formulations may be provided in the form of a bandage, wherein the formulation is incorporated into a gauze or other structure and brought into contact with the skin.

Administration of Antifungal Peptoids

An antifungal peptoid, as the active agent, may be administered to a subject alone or in a pharmaceutical composition that includes the active agent and a pharmaceutically acceptable carrier. The active agent is administered to a vertebrate, more preferably a mammal, such as a human patient, a companion animal, or a domesticated animal, in an amount effective to produce the desired effect. An antifungal peptoid may be administered in a variety of routes, including orally, parenterally, intraperitoneally, intravenously, intraarterially, transdermally, sublingually, intramuscularly, rectally, transbuccally, intranasally, liposomally, via inhalation, vaginally, intraoccularly, via local delivery by catheter or stent, subcutaneously, intraadiposally, intraarticularly, intrathecally, or in a slow release dosage form.

The formulations may be administered as a single dose or in multiple doses. Useful dosages of the active agents may be determined by comparing their in vitro activity and the in vivo activity in animal models. Methods for extrapolation of effective dosages in mice, and other animals, to humans are known in the art.

Dosage levels of the active agent in the pharmaceutical compositions of this disclosure may be varied so as to obtain an amount of the active agent which is effective to achieve the desired therapeutic response for a particular subject, composition, and mode of administration, without being toxic to the subject. The selected dosage level will depend upon a variety of factors including the activity of the particular compound of the present disclosure employed, or the ester, salt or amide thereof, the route of administration, the time of administration, the rate of excretion of the particular compound being employed, the duration of the treatment, other drugs, compounds and/or materials used in combination with the antifungal peptoid, the age, sex, weight, condition, general health and prior medical history of the subject being treated, and like factors well known in the medical arts.

Dosages and dosing regimens that are suitable for other prophylactic and therapeutic anti-fungal agents are likewise suitable for therapeutic or prophylactic administration of an antifungal peptoid. For example, dosages or dosing regimens in use for anti-fungal compounds, including, for example, flucytosine, may serve as guideposts for developing suitable animal and human dosages and dosing regimens. For example, an antifungal peptoid may be administered orally in an amount of at least 1 mg, at least 5 mg, at least 10 mg, at least 25 mg, at least 50 mg, at least 100 mg, or a higher amount at least once per day, as a medication, nutritional supplement, or food additive. In some embodiments, an antifungal peptoid may be administered orally in an amount of up to 50 mg, up to 100 mg, up to 200 mg, or up to 500 mg at least once per day, as a medication, nutritional supplement, or food additive. As another example, an antifungal peptoid may be administered in dosages ranging from at least 0.01 mg/kg body weight, at least 1 mg/kg body weight, or at least 5 mg/kg body weight and up to 5 mg/kg body weight, up to 10 mg/kg body weight, up to 20 mg/kg body weight, up to 50 mg/kg body weight, or up to 100 mg/kg body weight. In some embodiments, an antifungal peptoid may be administered in dosages in a form sufficient to provide a daily dosage of at least 0.01 mg/kg body weight, at least 1 mg/kg body weight, or at least 5 mg/kg body weight and up to 5 mg/kg body weight, up to 10 mg/kg body weight, up to 20 mg/kg body weight, up to 50 mg/kg body weight, or up to 100 mg/kg body weight. As a further example, an antifungal peptoid may be administered intravenously or intramuscularly in an amount between 5 mg and 100 mg at least once per day.

A physician or veterinarian having ordinary skill in the art may readily determine and prescribe the effective amount of the pharmaceutical composition required. For example, the physician could start doses of the antifungal peptoid employed in the pharmaceutical composition at levels lower than that required in order to achieve the desired therapeutic effect and gradually increase the dosage until the desired effect is achieved.

Methods of Treatment

An antifungal peptoid including γ-2 and/or β-5 may be used to treat or prevent fungal infections, particularly fungal infections. Exemplary fungal infections include, but are not limited to, an infection with a *Candida* species including, for example, *C. albicans, C. tropicalis, C. stellatoidea, C. glabrata, C. krusei, C. parapsilosis, C. guilliermondii, C. viswanathii,* or *C. lusitaniae*; an infection with *Rhodotorula mucilaginosa*; and/or an infection with *Cryptococcus* spp. including *C. neoformans, Cryptococcus gattii,* etc. This disclosure provides a therapeutic method of treating a subject suffering from an infection with a fungus by administering an antifungal peptoid to the subject. Therapeutic treatment is initiated after diagnosis or the development of symptoms of infection with a fungus.

An antifungal peptoid may also be administered prophylactically, to prevent or delay the development of infection with a fungus. Treatment that is prophylactic, for instance, may be initiated before a subject manifests symptoms of infection with a fungus. An example of a subject that is at particular risk of developing infection with a fungus is an immunocompromised person. Treatment may be performed before, during, or after the diagnosis or development of symptoms of infection. Treatment initiated after the development of symptoms may result in decreasing the severity of the symptoms of one of the conditions, or completely removing the symptoms. An antifungal peptoid may be introduced into the mammal at any stage of fungal infection.

Administration of an antifungal peptoid may occur before, during, and/or after other treatments. Such combination therapy may involve the administration of an antifungal peptoid during and/or after the use of other antifungal agents. The administration an antifungal peptoid may be separated in time from the administration of other antifungal agents by hours, days, or even weeks.

The compounds of the disclosure find utility in the treatment, control or prevention of fungal infection and disease not only in humans but also in animals. Compounds may be administered to companion animals, domesticated animals such as farm animals, animals used for research, or animals in the wild. Companion animals include, but are not limited to, dogs, cats, hamsters, gerbils and guinea pigs. Domesticated animals include, but are not limited to, cattle, horses, pigs, goats, and llamas. Research animals include, but are not limited to, mice, rats, dogs, apes, and monkeys. In one embodiment, the compound is administered to an animal, such as a companion animal or domesticated animal, that has been diagnosed with, or is exhibiting symptoms of, or is at risk of developing, a fungal infection. In another embodiment, the compound is administered in an animal or animal population that serves, may serve, or is suspected of serving as a fungal reservoir, regardless of the presence of symptoms. Administration may be, for example, part of a small or large scale public health infection control program. The compound may, for example, be added to animal feed as a prophylactic measure for reducing, controlling or eliminating fungal infection in a wild or domestic animal population. The compound may, for example, be administered as part of routine or specialized veterinary treatment of a companion or domesticated animal or animal population. It should be understood that administration of the compound may be effective to reduce or eliminate fungal infection or the symptoms associated therewith; to halt or slow the progression of infection or symptoms within a subject; and/or to control, limit or prevent the spread of infection within a population, or movement of infection to another population.

Nutritional Supplement and Food Additive

An antifungal peptoid may be packaged as a nutritional, health or dietary supplement (for example, in pill or capsule form). Additionally, an antifungal peptoid may be added to a food product to yield what is commonly referred to as a "nutriceutical" food or "functional" food. Foods to which an antifungal peptoid may be added include, without limitation, animal feed, cereals, yogurts, cottage cheeses, and other milk products, oils including hydrogenated or partially hydrogenated oils, soups and beverages. Antifungal peptoids having one or more lipophilic or hydrophobic substitutions are preferably incorporated into oily or fatty food products, to facilitate solubilization.

The present invention is illustrated by the following examples. It is to be understood that the particular examples, materials, amounts, and procedures are to be interpreted broadly in accordance with the scope and spirit of the invention as set forth herein.

EXAMPLES

Example 1

Figure 3A:
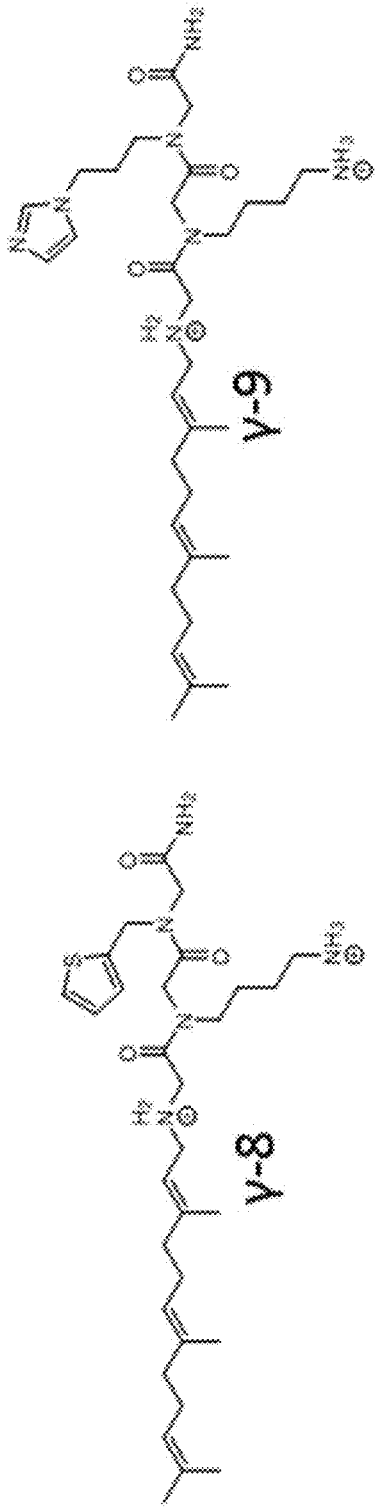
FIG. 3A shows Round 2 mSAR compounds ($\gamma$-8, $\gamma$-9, and $\gamma$-10) utilizing the farnesyl tail from Round 1 with varied aromatic heterocycles in the third position.
Figure 3B:
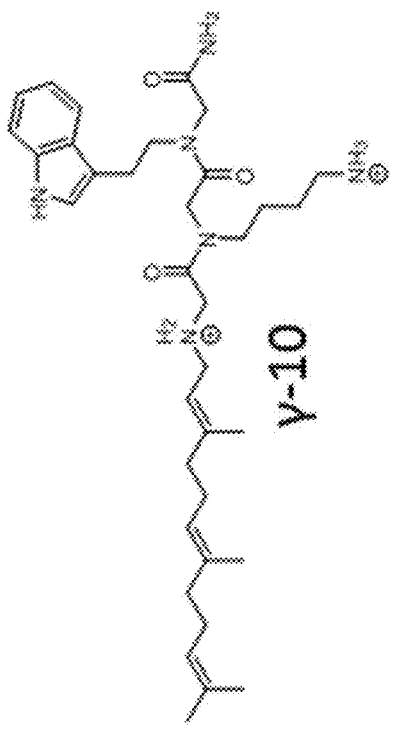
FIG. 3B shows calculated distribution coefficient (Log $D_{7.4}$), $C.$ $neoformans$ antifungal potency (MIC), and HepG2 liver cell toxicity ($TD_{50}$) for Round 2 (farnesyl tail) mSAR compounds. MW=molecular weight; Log $D_{7.4}$=calculated distribution coefficient at pH 7.4; MIC=minimum inhibitory concentration; $TD_{50}$=toxic dose 50%; SR=selectivity ratio ($TD_{50}$/MIC).
Figures 4A, 4B:
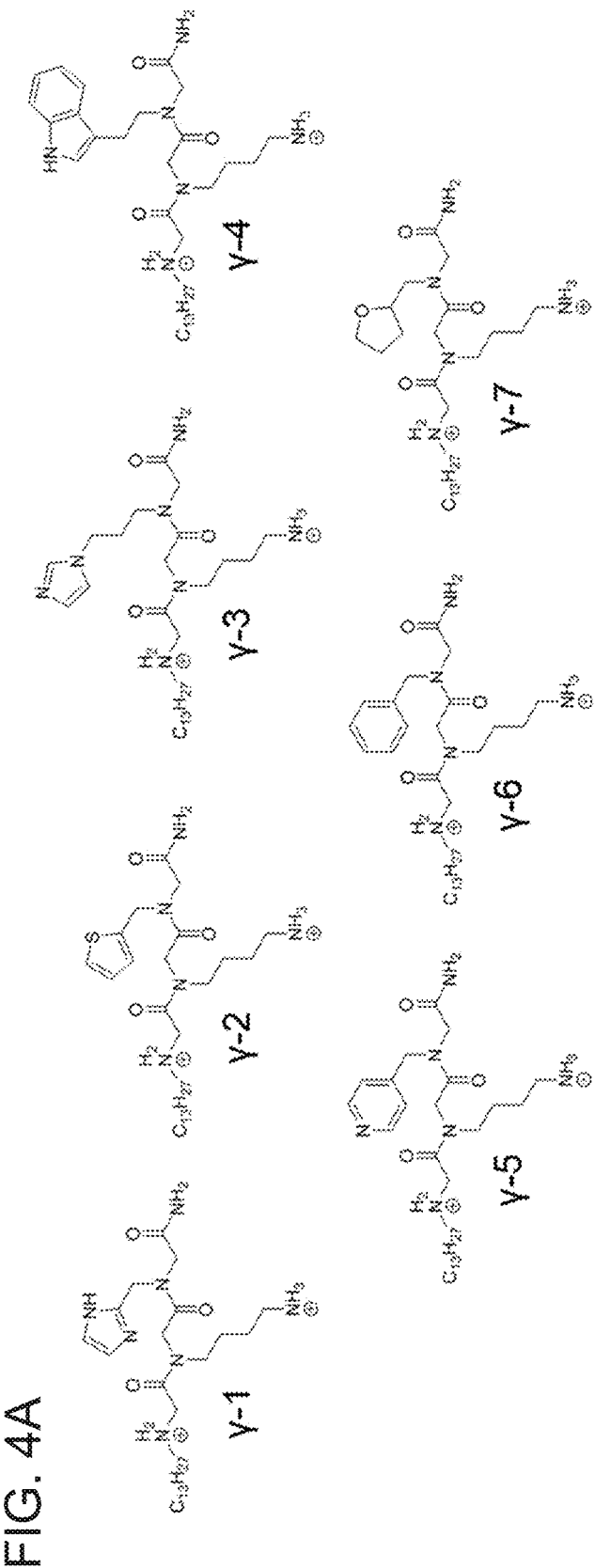
FIG. 4A shows Round 2 SAR compounds ($\gamma$-1, $\gamma$-2, $\gamma$-3, $\gamma$-4, $\gamma$-5, $\gamma$-6, and $\gamma$-7) utilizing the tridecyl tail from Round 1 with varied heterocyclic side chains in the third position.
FIG. 4B shows calculated distribution coefficient (c Log $D_{7.4}$), $C.$ $neoformans$ antifungal potency (MIC), and HepG2 liver cell toxicity (TD50) for Round 2 (tridecyl tail) SAR compounds. MW=molecular weight; c Log $D_{7.4}$=calculated distribution coefficient at pH 7.4; MIC=minimum inhibitory concentration; TD50=toxic dose 50%; SR=selectivity ratio (TD50/MIC).

This Example describes the iterative SAR optimization of previously identified antifungal peptoid, AEC5, resulting in two peptoids with significantly improved potency and toxicity profiles, γ-2 and β-5.
AEC5 Sarcosine Scan First, the pharmacological role of each of AEC5's three submonomers on $C.$ $neoformans$ potency and mammalian cell cytotoxicity was determined. The structure of AEC5 comprises three unique submonomers, each with a different chemical moiety (FIG. 1A). The N-terminus is a long hydrophobic tail, followed by a cationic ammonium side chain, and a C-terminal aromatic heterocycle. A sarcosine scan of AEC5 was completed, similar to an alanine scan of peptides, by synthesizing three AEC5 derivatives (termed $AEC5_{sar1-3}$) each with sarcosine in place of one of the submonomers (FIG. 1B). All compounds were synthesized on the solid phase using peptoid submonomer (Culf et al. $Molecules$ 2010, 15(8), 5282-5335) and traditional Fmoc techniques (Amblard et al. $Mol.$ $Biotechnol.$ 2006, 33(3), 239-254). The minimum inhibitory concentration (MIC) against $C.$ $neoformans$ and the cytotoxicity against HepG2 cells was then determined for these compounds, termed $AEC5_{sar1-3}$, as described previously (FIG. 1C). (Corson et al. $ACS$ $Med.$ $Chem.$ $Lett.$ 2016, 7(12).) Substituting sarcosine into any of the three positions had deleterious effects on antifungal potency but mixed effects of mammalian cytotoxicity. The largest change was observed for $AEC5_{sar1}$ where both potency and toxicity fell above the highest concentrations tested, 400 m/mL and 800 m/mL, respectively. These results are consistent with the previously reported importance of the alkyl chain in similar compounds. (Chongsiriwatana et al. $Antimicrob.$ $Agents$ $Chemother.$ 2011, 55(1), 417-420; Turkett et al. $ACS$ $Comb.$ $Sci.$ 2017, 19(4).) Substituting sarcosine in place of the cationic amino group of position two had a modest 2-fold decrease effect of antifungal potency compared to AEC5, but concomitantly increased the toxicity dose 50% ($TD_{50}$) by 2-fold, from 56.2 m/mL for AEC5 to 21.1 m/mL for $AEC5_{sar2}$. Sarcosine substitution at position two results in a substantial change in the calculated distribution coefficient, c Log $D_{7.4}$, from −1.18 for AEC5 to 1.44 for $AEC5_{sar2}$. This increase in hydrophobicity is the likely cause of increased toxicity for $AEC5_{sar2}$ and stresses the importance of this submonomer in mitigating mammalian toxicity. Interestingly, sarcosine substitution in place of an aromatic heterocycle at position three resulted in a substantial 8-fold change in antifungal potency with little effect on mammalian toxicity compared to AEC5. The mechanism of action of AEC5 is still being explored, and although it was hypothesized that this compound works the same way as other antifungal peptides and peptoids, through membrane disruption, the importance of this aromatic heterocycle in compound potency suggests that AEC5 may kill $C.$ $neoformans$ through a more complex mechanism of action. These data indicate that the alkyl tail is the most important pharmacophoric moiety in AEC5, this group was optimized during Round 1 of the following SAR studies.
Round 1 SAR AEC5 derivatives with sixteen, ten, and eight carbon alky tails in position 1, termed α-1, α-2, and α-3, respectively, were synthesized using peptoid submonomer methods (FIG. 2A). Given the polyene nature of the potent antifungal amphotericin B, the inclusion of polyene moieties in this position was expected to improve antifungal potency. The terpene aldehydes farnesal and citral were therefore attached to an N-terminal glycine in position one via reductive amination to afford compounds α-4 and α-5 respectively. The $C.$ $neoformans$ MIC of these compounds was evaluated (FIG. 2B), and significant decreases in potency were observed for compounds α-2 through α-5. The decrease in response to shortening the alkyl tail (compounds α-2 and α-3) was not surprising given literature precedent. (Chongsiriwatana et al. $Antimicrob.$ $Agents$ $Chemother.$ 2011, 55(1), 417-420; Turkett et al. $ACS$ $Comb.$ $Sci.$ 2017, 19(4).) Although increasing the length of the alkyl tail from thirteen to sixteen carbons yielded a compound with a 2-fold improvement in $C.$ $neoformans$ potency, it resulted in significantly increased toxicity against HepG2 liver cells. Neither polyene tail resulted in improved potency; however, the farnesyl tail did show a large decrease in toxicity (>800 μg/mL) while possessing a similar c Log $D_{7.4}$, albeit with a 16-fold decrease in antifungal potency. The significant decrease in toxicity was deemed to be important, and recovery antifungal potency through modification of the aromatic heterocycle in position three was attempted during Round 2 of SAR. Round 2 of SAR, further described below, using the farnesyl tail while varying heterocyclic side chains in the third position, resulted in compounds γ-8, γ-9, and γ-10, none of which showed improved potency over α-4 or AEC5 (FIG. 3). The use of the farnesyl tail was ultimately abandoned, and the alkyl tail in position one, the original tridecyl tail from AEC5, was used.
Round 2 SAR AEC5 derivatives containing a variety of aromatic heterocycles were synthesized by peptoid submonomer methods. These included imidazole derivatized compounds γ-1 and γ-3, compound γ-2 containing a thiophene side chain, γ-4 with an indole in this position, and γ-5 displaying a pyridyl ring (FIG. 4A). It is important to note that γ-5 required altered synthetic parameters published by Burkoth et al., $J.$ $Am.$ $Chem.$ $Soc.$ 2003, 125(29), 8841-8845, to negate the unwanted alkylation reaction at the pyridyl ring. These parameters were attained by using chloroacetic acid in place of bromoacetic acid and extending the length of amine coupling to account for the decreased leaving group ability of chlorine over bromine. Derivatives containing an aromatic phenyl side chain with no heteroatom (γ-6) and a non-aromatic heterocyclic tetrahydrofuran (γ-'7) were also synthesized. The $C.$ $neoformans$ potency and HepG2 toxicity of these compounds was determined (FIG. 4B). Derivatives γ-1, γ-3, γ-5 all showed 4- to 5-fold decreases in antifungal potency as well as a 2- to 4-fold decrease in mammalian cell toxicity. It is interesting to note that this decrease in potency and toxicity accompanies a decrease in c Log $D_{7.4}$, supporting our earlier findings that overall lipophilicity of short antimicrobial peptoids is linked to mammalian toxicity. (Turkett et al. ACS Comb. Sci. 2017, 19(4):229-233.) The substitution with a non-aromatic heterocycle (γ-7) gave a modest 2-fold decrease in antifungal potency and a 3-fold decrease in mammalian cell toxicity. Interestingly, placement of an aromatic phenyl ring with no heteroatom (γ-6) resulted in a 2-fold improvement in antifungal potency and no significant change in mammalian cell toxicity. These data, combined with data for $AEC5_{sar3}$ which has complete removal of the side chain in this position, suggest that perhaps the heteroatom here may play a role in selectivity of these compounds for C. neoformans over mammalian cells. A 2-fold improvement in antifungal potency was observed with three of the Round 2 derivatives; γ-2 with a thiophene side chain, γ-4 with an indole side chain, and γ-6, as mentioned, with a phenyl side chain. Two of these, γ-4 and γ-6 exhibited increased or unchanged mammalian cell toxicity compared to AEC5. However, γ-2 showed a decrease in HepG2 toxicity with a $TD_{50}$ of 79.3 µg/mL compared to 56.2 µg/mL for AEC5. With improvement in both potency and toxicity, a selectivity ratio of 25.3 was calculated for γ-2, compared to 8.9 for AEC5. A higher selectivity ratio, defined as the MIC divided by the $TD_{50}$, is indicative of a compound that is more selective for pathogen over mammalian cell. Data from Round 2 of SAR indicated that replacing the furan in position three with a thiophene greatly improved pathogen selectivity by increasing antifungal potency and decreasing mammalian toxicity. Therefore, the thiophene moiety was maintained in this position through Round 3 of SAR antifungal optimization.

Round 3 SAR

Figures 5A, 5B:
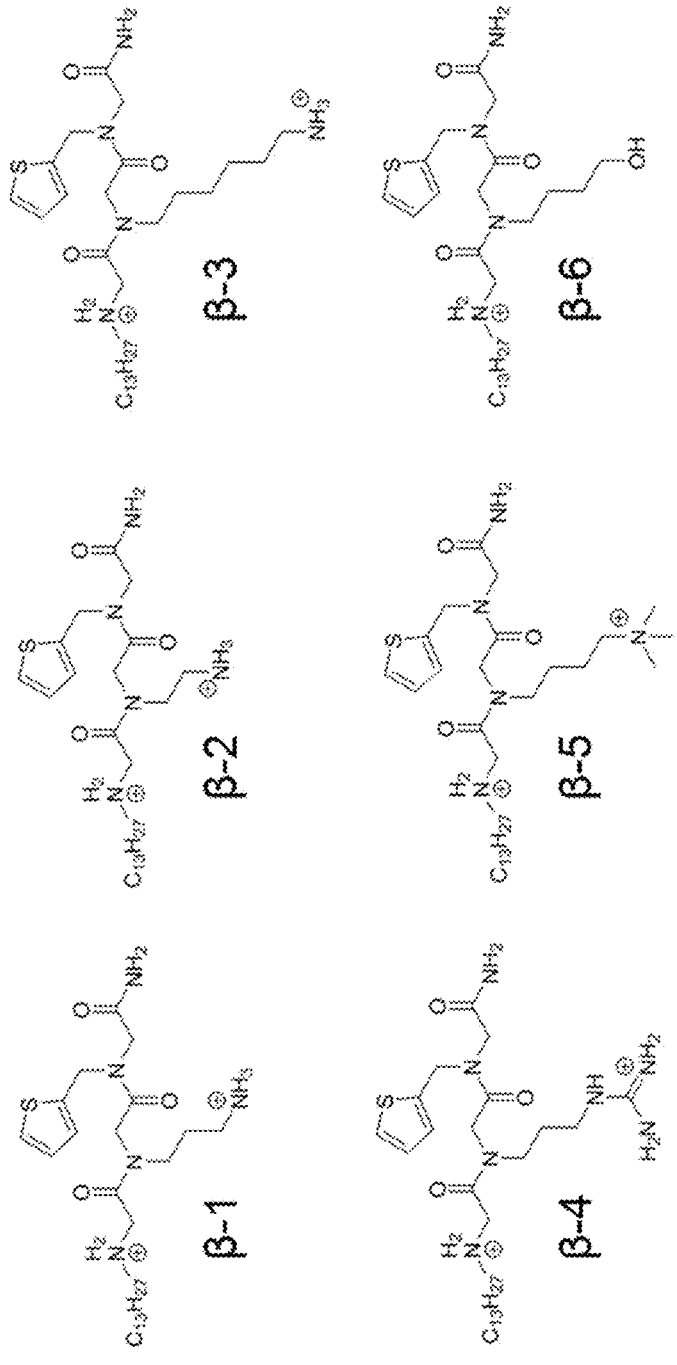
FIG. 5A shows Round 3 SAR compounds ($\beta$-1, $\beta$-2, $\beta$-3, $\beta$-4, $\beta$-5, and $\beta$-6) utilizing the tridecyl tail from Round 1 and the thiophene aromatic heterocyle from Round 2 with varied cationic moieties in position 2.
FIG. 5B shows calculated distribution coefficient (c Log $D_{7.4}$), $C.$ $neoformans$ antifungal potency (MIC), and HepG2 liver cell toxicity ($TD_{50}$) for Round 3 SAR compounds. MW=molecular weight; c Log $D_{7.4}$=calculated distribution coefficient at pH 7.4; MIC=minimum inhibitory concentration; $TD_{50}$=toxic dose 50%; SR=selectivity ratio ($TD_{50}$/MIC).
Figure 6:
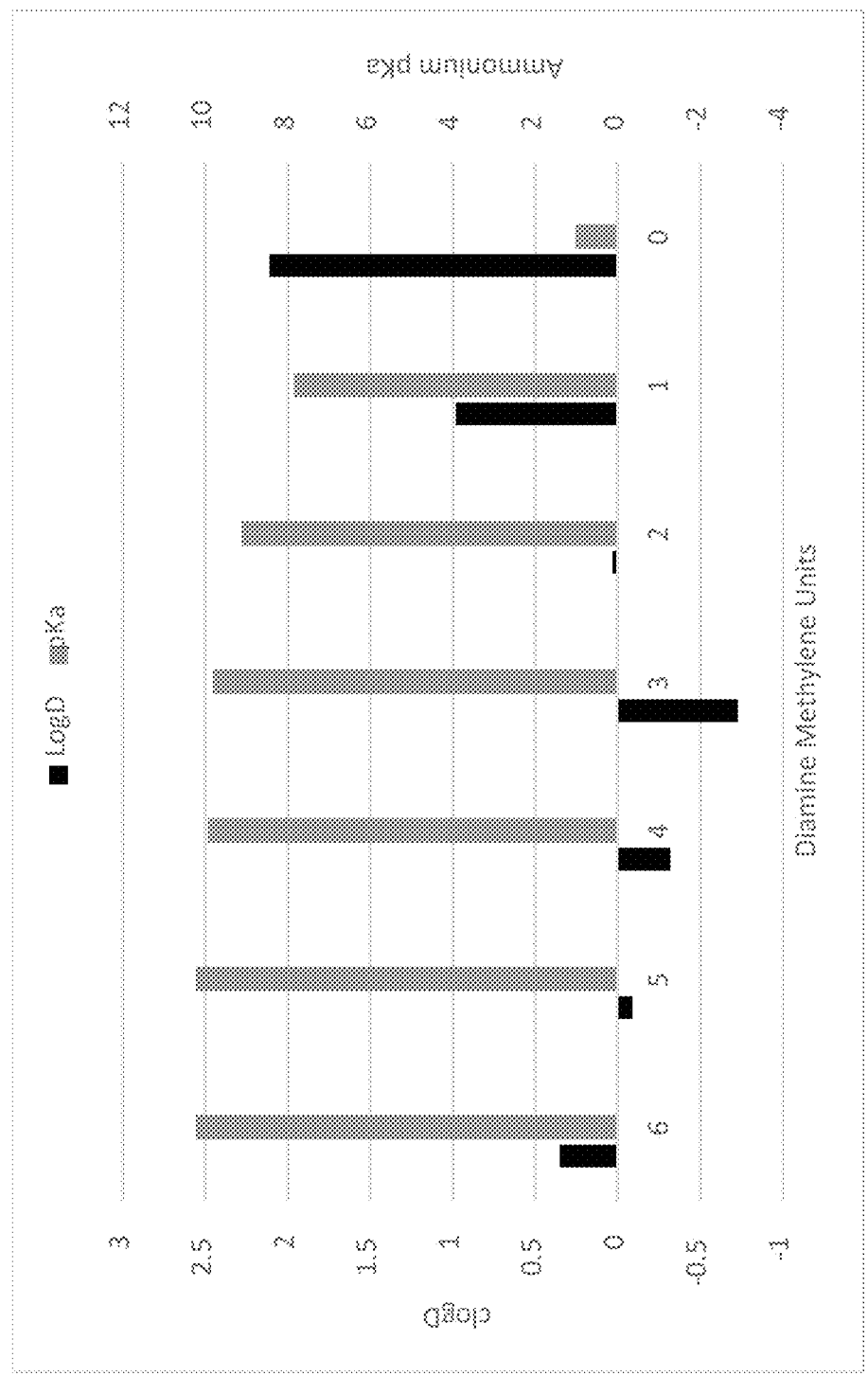
FIG. 6 shows calculated log D and $pK_a$ values for $\gamma$-2 derivatives with varying diamine methylene units in the $\beta$ position. All values were calculated using MarvinSketch.

Derivatives of γ-2 were synthesized containing various chemical moieties in position two. These derivatives include compounds with ammonium groups similar to γ-2 attached via fewer methylene units (β-1 and β-2), or more methylene units (β-3), as well as an arginine mimic (β-4), a trimethylammonium lysine mimic (β-5), and a non-cationic hydroxyl group (β-6) (FIG. 5A). This last derivative was synthesized and characterized to evaluate the efficacy of a hydrogen bonding moiety without cationic nature in position two. The MIC of β-6 falls off 4-fold compared to γ-2 while the toxicity against HepG2 cells becomes more than 2-fold worse (FIG. 5B). These data, combined with data from $AEC_{sar2}$, highlight the role of the cation in position two in improving C. neoformans potency, and perhaps more importantly, negating compound toxicity against mammalian cells. Bolt et al., Medchemcomm 2017, 8(5), 886-896, recently showed that the chain length between peptoid backbone and amino cation affects mammalian cytotoxicity and antibacterial activity, although this relationship varied between organisms. Modifying the side-chain length of γ-2 had little effect on antifungal activity, with only β-2, possessing the two carbon linker, showing a 2-fold decrease in potency. However, shortening the side-chain length was detrimental to mammalian cytotoxicity with β-1 (3 carbon linker) and β-2 having HepG2 cytotoxicity of 47.3 and 40.5 µg/mL, respectively. An interesting correlation between side-chain length and c Log $D_{7.4}$ was observed in the synthesized peptoids which was extrapolated out using distribution coefficients and $pK_a$ values calculated in MarvinSketch (ChemAxon, Budapest, Hungary, 2016, available on the world wide web at chemaxon.com) (FIG. 6). β-3 (6 carbon linker) had the highest distribution coefficient, as expected given the increased number of methylene units. As this side-chain is shortened to five, four (γ-2), or three methylenes (β-1), the distribution coefficient decreases, as anticipated. However, as this linker is shortened further to two methylenes (β-2) or further still to hypothetical compounds containing one or zero methylene units, the distribution coefficient rises sharply, indicating that these compounds are becoming more hydrophobic, even though they possess fewer carbon/hydrogen groups. Given that the calculated distribution coefficient factors in compound ionization, an explanation for this trend can be obtained by observing the calculated $pK_a$ values for the amino cation. These values remain relatively constant around a $pK_a$ of 10 for compounds possessing side-chain linker lengths of 3-6 carbons. As the linker length becomes shorter than three, however, the calculated $pK_a$ begins to drop, meaning that this side-chain amino group becomes less ionized at neutral pH. Given these observations regarding increased mammalian cytotoxicity with complete removal of the cation in position 2, it was hypothesized that this loss of ionization with shorter side-chain length makes peptoids more cytotoxic. This hypothesis was further confirmed by evaluating trimethylated γ-2 derivative, β-5, which is permanently ionized; this compound exhibited no change in MIC but showed further improvement to mammalian cytotoxicity with a $TD_{50}$ of 91.2 µg/mL.

Yield and ESI-MS Evaluation

Electrospray ionization mass spectroscopy (ESI-MS) was performed as described in Ren et al. J. Am. Soc. Mass Spectrom. (2016) 27: 646. Yield and ESI-MS results are provided in Table 1.

Broad Toxicity Evaluation

One of the most significant shortcomings of current antifungals is their broad toxicity. The broad toxicity of the most promising antifungal peptoids developed through SAR against NIH/3T3 mouse fibroblasts and human erythrocytes was, therefore, evaluated, in addition the HepG2 testing already completed. As seen with liver cells, both γ-2 and β-5 exhibited decreased toxicity towards NIH/3T3 mouse fibroblasts, with selectivity ratios improving from 8 for AEC5 to 21 and 37 for γ-2 and β-5, respectively. Interestingly, both γ-2 and β-5 had slightly higher levels of hemolysis compared to AEC5. The $HC_{10}$ value reported here for AEC5 differs from that published previously. Given that human erythrocytes are primary and originate from different donors, AEC5 was reevaluated along with γ-2 and β-5 to provide the most accurate hemolytic data. Maximum hemolysis at 100 µg/mL ($H_{max}$) further confirmed that the AEC5 derivatives tested here are more hemolytic than the original peptoid. Although slightly increased hemolytic properties are a drawback for γ-2 and β-5, these compounds nonetheless maintain improved selectivity ratios for human erythrocytes compared to AEC5 due to their improved potency against C. neoformans.

Materials and Methods

Reagents were purchased from Fisher Scientific (Waltham, Mass.), Alfa Aesar (Haverhill, Mass.), Amresco (Solon, Ohio), TCI America (Portland, Oreg.), Anaspec (Fremont, Calif.), EMD Millipore (Billerica, Mass.), Peptides International (Louisville, Ky.), and Chem-Implex (Wood Dale, Ill.). Human red blood cells (hRBCs) were acquired from Innovative Research (Novi, Mich.). Synthesis of N-(tert-butoxycarbonyl)-1,4-diaminobutane, N-(tert-butoxycarbonyl)-1,3-diaminopropane, and N-(tert-butoxycarbonyl)-1,2-diaminoethane were all done as reported previously. (Fisher et al. ACS Comb. Sci. 2016, 18(6); Corson et al. ACS Med. Chem. Lett. 2016, 7(12).) All mass spectra were acquired on a Waters Synapt HDMS QToF with Ion Mobility and all NMR spectra were acquired on a JOEL ECA 500 NMR spectrometer. All fluorescence and absorbance readings were acquired on a Spectramax M5 or M2 plate reader. c Log $D_{7.4}$ and $pK_a$ were calculated using MarvinSketch Calculator Plugins (ChemAxon, Budapest, Hungary, 2016, available on the world wide web at chemaxon.com).

Submonomer Synthesis. Synthesis of O-(tert-butyldimethylsilyl)-4-amino-1-butanol Synthesis of O-(tert-butyldimethylsilyl)-4-amino-1-butanol was adapted from a previous procedure. (Corson et al. ACS Med. Chem. Lett. 2016, 7(12).) Briefly, 4-amino-1-butanol (1.93 mL, 0.021 mol) and imidazole (2.72 g, 0.040 mol) were dissolved in 20 mL $CH_2Cl_2$. Tert-butyldimethylchlorosilane (TBDMS-Cl, 3.17 g, 0.021 mol) was dissolved in 10 mL $CH_2Cl_2$ and slowly added to the ethanolamine/imidazole mixture over 5 minutes. The reaction was stirred at room temperature for 1 hour. Deionized water (20 mL) was added, the organic layer collected, and the aqueous layer washed twice more with $CH_2Cl_2$. The combined organic layers were dried over $CaCl_2$) and concentrated in vacuo to yield a pale yellow oil (1.4 g; 33% yield). ESI $[M+H]^{+1}$ expected 204.18 Daltons (Da), observed 204.13 Da.

Synthesis of N-(tert-butoxycarbonyl)-1,6-diaminohexane

Concentrated hydrochloric acid (1.91 mL, 0.0229 mol) was added to 30 mL methanol (MeOH) and cooled to 0° C. 1,6-diaminohexane (2.66 g, 0.0229 mol) was added to the acidified methanol and stirred for 20 minutes. Deionized water (10 mL) was added stirred for 30 minutes. Di-tert-butyl dicarbonate (7.90 mL, 0.0344 mol) in MeOH (40 mL) was added dropwise over 10 minutes to the diamine solution. The reaction was allowed to come to room temperature over 1 hours with stirring. The solvent was removed in vacuo and the resulting solid washed with diethyl ether (3×30 mL). Sodium hydroxide (1 M) was added and the product was extracted 2 times with $CH_2Cl_2$. The organic layers were combined, washed with brine, dried over $CaCl_2$), and concentrated in vacuo to yield a white solid (3.31 g, 66.9% yield). ESI $[M+H]^{+1}$ expected 217.33 Da, observed 217.18 Da.

Synthesis of N-monomethoxytrityl-1,3-diaminopropane 1,3-diaminopropane (2.28 g; 30.8 mmol) was added to $CH_2Cl_2$ (9 mL) and stirred on ice for 10 minutes. Monomethoxytrityl chloride (1.050 g; 3.40 mmol) was added in five aliquots over 15 minutes. The reaction was removed from ice, allowed to warm to room temperature, and stirred for 4 hours. Solvent was removed in vacuo and the remaining residue dissolved in 1:1 water:$CH_2Cl_2$ containing 1% triethylamine. This mixture was extracted twice with $CH_2Cl_2$ and the combined organic layers dried over magnesium sulfate. Solvent was removed in vacuo to give the product as a red oil (1.119 g; 95.0% yield). This compound was used for peptoid synthesis without further purification. ESI $[M+H]^{+1}$ expected 361.23 Da, observed 361.27 Da.

Synthesis of N-monomethoxytrityl-1,4-diaminobutane 1,4-diaminobutane (2.73 g; 31.0 mmol) was added to $CH_2Cl_2$ (9 mL) and stirred on ice for 10 minutes. Monomethoxytrityl chloride (1.050 g; 3.40 mmol) was added in five aliquots over 15 minutes. The reaction was removed from ice, allowed to warm to room temperature, and stirred for 4 hours. Solvent was removed in vacuo and the remaining residue dissolved in 1:1 water:$CH_2Cl_2$ containing 1% triethylamine. This mixture was extracted twice with $CH_2Cl_2$ and the combined organic layers dried over magnesium sulfate. Solvent was removed in vacuo to give the product as a red oil (1.196 g; 97.6% yield). This compound was used for peptoid synthesis without further purification. ESI $[M+H]^{+1}$ expected 361.23 Da, observed 361.27 Da.

Procedures for Solid-Phase Synthesis. Peptoid Synthesis.

Peptoids were synthesized using standard peptoid submonomer methods. (Zuckermann et al. J. Am. Chem. Soc. 1992, 114(26), 10646-10647.) For each synthesis, deprotected Rink Amide polystyrene resin (0.8 mmol/g) was used as the solid support. For installation of a peptoid submonomer, the resin was first treated with 2 M bromoacetic acid in anhydrous DMF (1.5 mL) and 3.2 M diisopropylcarbodiimide (DIC) in anhydrous DMF (1.5 mL). The mixture was microwaved for a total of 30 seconds at 10% power (100 kW) and then gently rocked for 15 minutes before aspirating the solution and washing the resin 3 times with DMF. A 2 M solution of the amine needed for the appropriate side chain in anhydrous DMF (3 mL) was then added and the mixture was again microwaved at 10% power for a total of 30 seconds, rocked for 15 minutes, and washed 3× with DMF. The amines used for the synthesis of each peptoid may be found in FIG. 7. Each step was verified colorimetrically by ninhydrin testing. The synthesis of peptoids requiring specialized procedures that deviate from those described above are detailed below.

Amino Acid Coupling.

Installation of sarcosine was achieved for $AEC5_{sar1-3}$ using Fmoc-Sar-OH. Briefly, Fmoc-Sar-OH (199 mg; 0.64 mmol) and N,N,N',N'-tetramethyl-O-(1H-benzotriazol-1-yl) uronium hexafluorophosphate (HBTU; 242 mg; 0.64 mmol) were combined in 5% N-methylmorpholine (NMM) in DMF and allowed to react for 10 minutes prior to addition to the resin. After reacting with the resin for 1 hour with gentle rocking, the solution was aspirated and the resin was washed 3 times with DMF. Removal of the Fmoc group was then completed by treating with 20% piperidine in DMF twice, 10 minutes each. Each step was verified colorimetrically by ninhydrin testing.

Reductive Amination.

Attachment of farnesyl and citryl alkyl tails in the synthesis of compounds α-3, α-4, γ-9, γ-10, and γ-11 was achieved by reductive amination. Following attachment of the first two peptoid submonomers, Fmoc-Gly-OH was attached and deprotected as described above for sarcosine. Terpene alkyl tails were then added by treating with either farnesal or citral (1.58 mmol) in 9:1 DMF:methanol. The reaction was rocked gently at 37° C. for 20 hours. Reduction was accomplished with $NaBH_4$ (30 mg; 0.79 mmol) for 1 hour at 25° C. warming to 37° C. hours over 3 hours before washing with DMF.

Synthesis of γ-5

Due to the reactivity of the pyridinyl side chain, γ-5 was synthesized following slightly modified submonomer conditions as previously described. (Burkoth et al. J. Am. Chem. Soc. 2003, 125(29), 8841-8845.) Briefly, Rink amide resin was prepared, coupled with bromoacetic acid, and coupled with 2-aminomethyl pyridine as described above. The subsequent acylation reactions for this compound were achieved by treating the resin with 0.4 M chloroacetic acid (1.7 mL) and 2 M DIC (0.4 mL) in anhydrous DMF and tumbling at 35° C. for 5 minutes. Amine couplings following chloroacylation were accomplished using 2 M amine solution in DMF (3 mL) at 35° C. for 90 minutes.

Synthesis of β-4

Peptoid synthesis was completed as described above using N-monomethoxytrityl-1,3-diaminopropane as the amine in position two to provide an orthogonal protecting group in this position. While still on the solid phase, the N-terminus of this peptoid was protected by treating with Boc anhydride (368 µL; 1.6 mmol; 10 eq) in 5% NMM in DMF (5 mL) for 1 hour with gentle rocking. Resin was washed with DMF and $CH_2Cl_2$. The monomethoxytrityl protecting group was removed from the δ-amine in position two by treating 3× with 1% trifluoroacetic acid (TFA) in $CH_2Cl_2$ (5 mL) for 10 minutes, followed by washing with $CH_2Cl_2$ and DMF. Resin amines were freebased by treating with 5% NMM in DMF for 5 minutes prior to guanidinylation with pyrazole carboxamidine HCl (233 mg; 1.6 mmol; 10 eq) and catalyst dimethylaminopyridine (DMAP; 19.5 mg; 0.16 mmol; 1 eq) in 5% NMM in DMF (5 mL) for 20 hours at 25° C. with gentle rocking. Resin was washed with DMF and $CH_2Cl_2$. The N-terminal Boc group was subsequently removed during compound cleavage from the resin.

Synthesis of β-5

Peptoid synthesis was completed as described above using N-monomethoxytrityl-1,4-diaminobutane as the amine in position two to provide an orthogonal protecting group in this position. While still on the solid phase, the N-terminus of this peptoid was protected by treating with Boc anhydride (368 µL; 1.6 mmol; 10 eq) in 5% NMM in DMF (5 mL) for 1 hour with gentle rocking. Resin was washed with DMF and $CH_2Cl_2$. The monomethoxytrityl protecting group was removed from the ε-amine in position two by treating 3× with 1% trifluoroacetic acid (TFA) in $CH_2Cl_2$ (5 mL) for 10 minutes, followed by washing with $CH_2Cl_2$ and DMF. Resin amines were free based by treating with 5% NMM in DMF for 5 minutes prior to trimethylation with methyl iodide (99.6 µL; 1.6 mmol; 10 eq) and $Cs_2CO_3$ (130 mg; 0.4 mmol; 2.5 eq) in DMF (5 mL) for 20 hours at 25° C. with gentle rocking. Resin was washed with DMF, water, DMF, and $CH_2Cl_2$. The N-terminal Boc group was subsequently removed during compound cleavage from the resin.

Peptoid Purification and Characterization.

Prior to cleavage from the resin, DMF was removed by washing the resin 3 times with $CH_2Cl_2$ and aspirating for 10 minutes. Removal of the peptoid from the resin was accomplished by rocking the resin in 95% trifluoroacetic acid (TFA; 6.65 mL), 2.5% triisopropylsilane (TIS; 0.175 mL), and 2.5% $H_2O$ (0.175 mL) for 1 hour. The solution was then filtered to separate the compound from the resin and TFA was bubbled off. Peptoids were purified via RP-HPLC using a Varian Prepstar SD-1 with Supelco Ascentis C18 column and a gradient of water to acetonitrile containing 0.05% trifluoroacetic acid. Purified products were lyophilized to give each compound as a white powder.

Compound Testing. Minimum Inhibitory Concentration Testing.

The minimum inhibitory concentration (MIC) was determined against *C. neoformans* H99S (serotype A lab strain) as previously described. (Corson, et al. *ACS Med. Chem. Lett.* 2016, 7(12).) All MIC assays were carried out following CLSI guidelines. (CLSI. *Reference method for broth dilution antifungal susceptibility testing of yeasts; approved standard-third edition; CLSI document M27-A3*; Clinical and Laboratory Standards Institute: Wayne, Pa.) Briefly, the organism to be tested was streaked from frozen stock for isolation and incubated for 96 hours. A 5 mL solution of 0.85% saline was inoculated with 1-2 colonies of the organism of interest, and the inoculated solution was vortexed for one minute. The optical density at 530 nanometers (nm) was acquired on a spectrophotometer and adjusted through addition of saline or cells to obtain an $OD_{530nm}$ of 0.15 to 0.25. A 1:100 solution of Roswell Park Memorial Institute (RPMI) media containing 3-morpholinopropane sulfonic acid (MOPS; 0.1 M) and cells was made by adding 0.100 mL of saline inoculated with cells to 9.9 mL of RMPI. The solution was vortexed and used to make a 1:20 solution by adding and vortexing 0.5 mL of the 1:100 solution to 9.5 mL of RPMI+0.1 M MOPS. (This was repeated twice to make a total of 20 mL of 1:20 RPMI+ cells.)

Two-fold serial dilutions of peptoid were prepared in water at 100 times the concentration to be tested. In a 96-well plate, 198 µL of 1:20 RPMI+cells was placed in each well followed by 2 µL of 100-times compound or vehicle control in triplicate. The plate was incubated at 35° C. for 72 hours. For viability analysis, 20 µL of PrestoBlue was added to each well, the plate incubated for 8 hours, and the fluorescent intensity of each well measured (Ex. 555 nm; Em. 585 nm). All triplicate assays were repeated twice on different days.

Mammalian Cytotoxicity Testing.

NIH/3T3 mouse fibroblasts and HepG2 hepatocarcinoma cells, cells were grown in DMEM containing 10% FBS at 37° C. and 5% $CO_2$ atmosphere. For cytotoxicity testing, cells were seeded into 96-well plates in phenol red free DMEM containing 10% FBS and incubated for 2 hours to allow cell attachment. Cells were then treated with varying concentrations of peptoid or vehicle control. After 72 hours incubation, 3-(4,5-dimethylthiazol-2-yl)-2,5-diphenyltetrazolium bromide (MTT; 20 µL; 5 mg/mL) was added to each well and the plate incubated for 3.5 hours. Media was removed from each well and 100 µL of DMSO was added and the plate incubated at 37° C. for 10 minutes. The absorbance at 570 nm was then read on a spectrophotometer, percent inhibition determined, and $TD_{50}$ calculated using GraFit. All triplicate assays were repeated twice on different days.

Hemolytic Activity.

The hemolytic activity of peptoids against human red blood cells (hRBCs) was done as previously described. (Murugan et al. *Bioorg. Med. Chem. Lett.* 2013, 23(16), 4633-4636.) Briefly, hRBCs were washed 3× with PBS (11.8 mM phosphate; 140.4 mM NaCl; pH 7.4) by centrifugation (10 minutes at 1000×g). Cells were resuspended in PBS and 100 µL aliquots placed into individual wells of a 96-well plate. Peptoid solutions (2-fold serial dilution in PBS; 400-3.13 µg/mL final) were added to the wells. A negative control was prepared by adding PBS with no peptoid to the hRBCs and a positive control was prepared by adding 1% Triton X-100 to the hRBCs. The plate was incubated at 37° C. for 1 hour, centrifuged at 1000×g for 10 minutes, and 5 µL of supernatant transferred into 95 µL of PBS in a new 96-well plate. Released hemoglobin was measured by reading the absorbance at 405 nm on a spectrophotometer. All triplicate assays were repeated twice on different days. Percent hemolysis was calculated as follows:

$$\% \text{ hemolysis} = \frac{(OD_{405nm} \text{ sample} - OD_{405nm} neg. \text{ control})}{(OD_{405nm} pos. \text{ control} - OD_{405nm} \text{ sample})} \times 100$$

The Hill Slope (H) and $HC_{50}$ was determined using GraFit and $HC_{10}$ was calculated from $HC_{50}$ using the following equation:

$$HC_{10} = HC_{50}[10\%/(100\%-10\%)]^{1/H}$$

NMR Analysis

O-(tert-butyldimethylsilyl)-4-amino-1-butanol

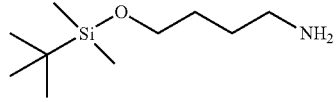

$^1$H-NMR (500 MHz, CDCl$_3$) δ 0.01 (s, 6H), δ 0.853 (s, 9H), δ 1.51 (m, 4H), δ 2.7 (t, 2H, J=5.49 Hz), δ 3.59 (t, 2H, J=5.49 Hz), δ 3.89 (s, 2H).

N-(tert-butoxycarbonyl)-1,6-diaminohexane

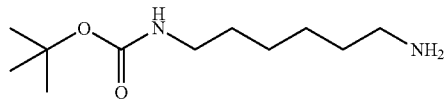

$^1$H-NMR (500 MHz, CDCl$_3$) δ 1.29 (m, 4H), δ 1.43 (m, 13H), δ 2.64 (t, 2H, J=7.45 Hz), δ 3.07 (m, 4H), δ 4.54 (s, 1H).

N-monomethoxytrityl-1,3-diaminopropane

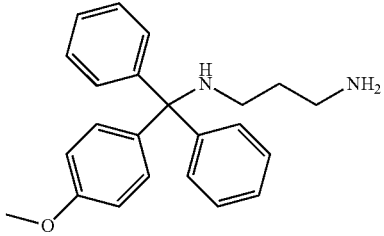 [SMILES: COc1ccc(C(NCCCN)(c2ccccc2)c2ccccc2)cc1]

$^1$H-NMR (500 MHz, CDCl$_3$) δ 1.44 (s, 2H), δ 1.61 (quint, 2H, J=6.9 Hz), δ 2.18 (t, 2H, J=6.9 Hz), δ 2.77 (t, 2H, J=6.6 Hz), δ 3.77 (s, 3H) δ 6.80 (m, 2H), δ 7.17 (m, 2H), δ 7.24 (m, 4H), δ 7.36 (m, 2H), δ 7.45 (m, 4H).

N-monomethoxytrityl-1,4-diaminobutane

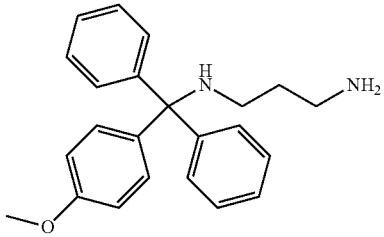 [SMILES: COc1ccc(C(NCCCN)(c2ccccc2)c2ccccc2)cc1]

$^1$H-NMR (500 MHz, CDCl$_3$) δ 1.52 (m, 4H), δ 2.08 (s, 1H), δ 2.13 (t, 2H, J=6.3 Hz), δ 2.70 (t, 2H, J=6.9 Hz), δ 2.86 (m, 2H), δ 3.77 (s, 3H) δ 6.80 (m, 2H), δ 7.16 (m, 2H), δ 7.25 (m, 4H), δ 7.35 (t, 2H, J=9.1 Hz), δ 7.45 (t, 4H, J=7.5 Hz).

γ-2

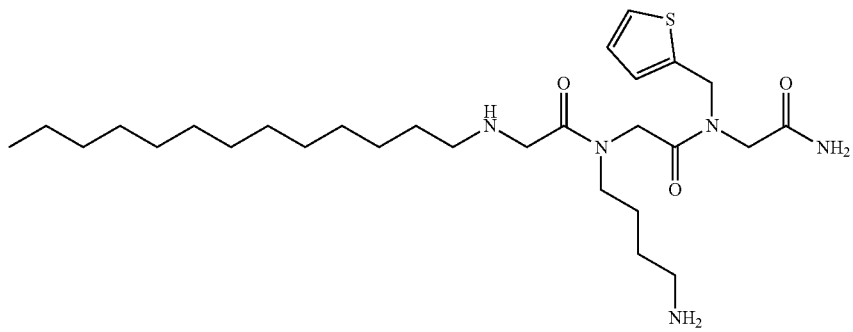 [SMILES: CCCCCCCCCCCCCNCC(=O)N(CCCCN)CC(=O)N(CC(N)=O)Cc1cccs1]

¹H-NMR (500 MHz, D₂O) δ 7.06 (m, 1H), 6.85 (m, 1H), 6.74 (m, 1H), 4.51 (s, 1H), 4.32 (s, 1H), 4.14 (s, 1H), 4.01 (s, 2H), 3.66 (s, 1H), 3.26 (s, 2H), 2.83 (m, 4H), 1.50 (m, 6H), 1.10 (m, 22H), 0.71 (t, J=7.2 Hz, 3H). ¹³C NMR (D₂O, 126 MHz) δ 171.6, 169.3, 167.2, 138.4, 127.7, 126.6, 125.8, 49.0, 48.9, 48.6, 48.2, 47.6, 47.5, 47.4, 46.8, 39.1, 32.0, 29.8, 29.5, 29.1, 26.4, 26.3, 25.1, 24.6, 24.1, 23.7, 22.6, 13.9.

TABLE 1

Yield and ESI-MS information for each synthesized peptoid.

| Compound | Yield (mg) | Yield (%) | ESI [M + H]⁺ expected (g/mol) | ESI [M + H]⁺ observed (g/mol) |
|---|---|---|---|---|
| AEC5sar1 | 17.8 | 23.8% | 354.4 | 354.2 |
| AEC5sar2 | 79.8 | 86.3% | 465.7 | 465.9 |
| AEC5sar3 | 31.7 | 34.8% | 456.7 | 456.4 |
| α-1 | 17.1 | 15.8% | 564.8 | 564.4 |
| α-2 | 5.9 | 12.4% | 480.7 | 480.6 |
| α-3 | 7.3 | 16.1% | 452.6 | 452.6 |
| α-4 | 4.0 | 7.6% | 544.8 | 544.3 |
| α-5 | 2.5 | 5.3% | 476.6 | 476.5 |
| γ-1 | 4.0 | 3.9% | 522.8 | 522.4 |
| γ-2 | 28.7 | 27.5% | 538.8 | 538.4 |
| γ-3 | 2.1 | 3.9% | 550.8 | 550.4 |
| γ-4 | 4.9 | 8.8% | 585.9 | 585.4 |
| γ-5 | 4.3 | 5.1% | 533.8 | 533.3 |
| γ-6 | 14.4 | 14.0% | 532.8 | 532.4 |
| γ-7 | 13.7 | 13.4% | 526.8 | 526.3 |
| γ-8 | 4.4 | 8.2% | 560.8 | 560.3 |
| γ-9 | 3.7 | 6.7% | 572.8 | 572.4 |
| γ-10 | 2.4 | 4.2% | 607.9 | 607.4 |
| β-1 | 32.2 | 31.5% | 524.8 | 524.3 |
| β-2 | 47.6 | 47.6% | 510.8 | 510.3 |
| β-3 | 29.3 | 26.7% | 566.4 | 566.5 |
| β-4 | 6.9 | 6.3% | 566.8 | 566.5 |
| β-5 | 17.7 | 15.8% | 580.9 | 580.4 |
| β-6 | 2.0 | 2.3% | 539.8 | 539.3 |

The complete disclosure of all patents, patent applications, and publications, and electronically available material (including, for instance, nucleotide sequence submissions in, for example, GenBank and RefSeq, and amino acid sequence submissions in, for example, SwissProt, PIR, PRF, PDB, and translations from annotated coding regions in GenBank and RefSeq) cited herein are incorporated by reference. In the event that any inconsistency exists between the disclosure of the present application and the disclosure(s) of any document incorporated herein by reference, the disclosure of the present application shall govern. The foregoing detailed description and examples have been given for clarity of understanding only. No unnecessary limitations are to be understood therefrom. The invention is not limited to the exact details shown and described, for variations obvious to one skilled in the art will be included within the invention defined by the claims.

What is claimed is:

1. A composition comprising γ-2:

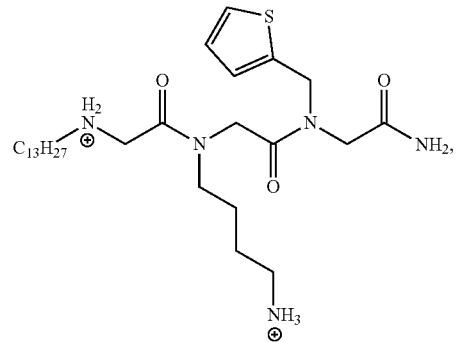

or β-5:

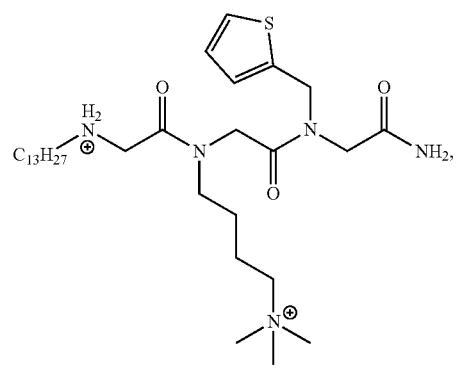

or both γ-2 and β-5.

2. The composition of claim 1, wherein the composition comprises a pharmaceutical composition.

3. The composition of claim 2, wherein the composition comprises a pharmaceutically acceptable carrier.

4. A method of treating a fungal infection in a subject comprising administering to a subject the composition of claim 3, wherein the fungal infection comprises infection with *Cryptococcus* spp.

5. The method of claim 4, wherein the subject is an animal or a human.

6. The method of claim 4, wherein the *Cryptococcus* spp. comprise *Cryptococcus neoformans*, or *Cryptococcus gattii*, or both.

7. The method of claim 4, the method further comprising administering an effective amount of a systemic antifungal agent or a topical antifungal agent.

8. A compound having the formula:

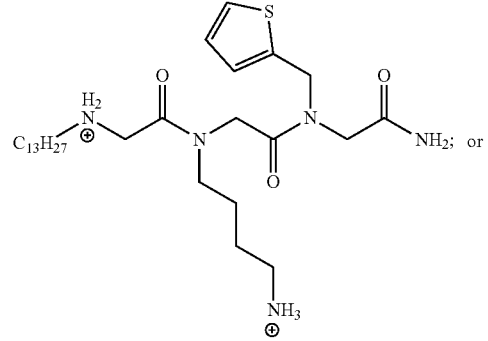

-continued
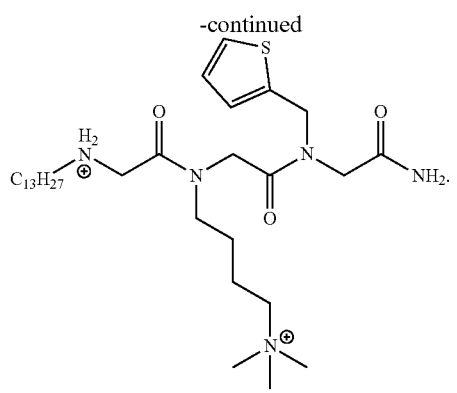
9. A method of making a compound of claim 8, wherein the method comprises submonomer peptoid synthesis.
* * * * *